US009101459B2

(12) United States Patent
Wexler et al.

(10) Patent No.: US 9,101,459 B2
(45) Date of Patent: Aug. 11, 2015

(54) APPARATUS AND METHOD FOR HIERARCHICAL OBJECT IDENTIFICATION USING A CAMERA ON GLASSES

(71) Applicants: Yonatan Wexler, Jerusalem (IL); Amnon Shashua, Mevasseret Zion (IL)

(72) Inventors: Yonatan Wexler, Jerusalem (IL); Amnon Shashua, Mevasseret Zion (IL)

(73) Assignee: OrCam Technologies, Ltd., Jerusalem (IL)

( * ) Notice: Subject to any disclaimer, the term of this patent is extended or adjusted under 35 U.S.C. 154(b) by 0 days.

(21) Appl. No.: 14/137,446

(22) Filed: Dec. 20, 2013

(65) Prior Publication Data

US 2014/0267650 A1 Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*H04N 7/18* (2006.01)
*A61F 9/08* (2006.01)
(Continued)

(52) U.S. Cl.
CPC . *A61F 9/08* (2013.01); *G06F 3/011* (2013.01); *G06F 3/16* (2013.01); *G06F 17/2765* (2013.01); *G06K 9/00221* (2013.01); *G06K 9/00288* (2013.01); *G06K 9/00671* (2013.01); *G06K 9/74* (2013.01); *G08B 3/10* (2013.01);
(Continued)

(58) Field of Classification Search
CPC ....................................................... A61F 9/08
USPC ........................................................... 348/62
See application file for complete search history.

(56) References Cited

U.S. PATENT DOCUMENTS

| 6,115,482 A | 9/2000 | Sears et al. |
| 2005/0208457 A1 | 9/2005 | Fink et al. |

(Continued)

FOREIGN PATENT DOCUMENTS

| EP | 2065871 | 6/2009 |
| EP | 2 490 155 A1 | 8/2012 |

OTHER PUBLICATIONS

Lai, Chin-Lun et al.; "An Integrated Portable Vision Assistant Agency for the Visual Impaired People," 2009 IEEE Internationai Conference on Control and Automation, Christchurch, New Zealand, Dec. 9-11, 2009 (6 pages).

(Continued)

*Primary Examiner* — Richard Torrente
(74) *Attorney, Agent, or Firm* — Finnegan, Henderson, Farabow, Garrett & Dunner LLP

(57) ABSTRACT

Apparatuses and a method are provided for providing environmental information to a user, who may be visually impaired. In one implementation, a method is provided for receiving real time image data including an object within the user environment. The method includes identifying a hand-related trigger in the image data. Upon identifying the hand-related trigger, the method includes executing a first search in the image data in an attempt to identify at least one object from a first category of objects. After initiating the first search, the method includes executing a second search in the image data in an attempt to identify at least one object from a second category of objects that differs from the first. The method also includes outputting audible feedback to the user associated with information related to an object or objects identified in the image data.

25 Claims, 23 Drawing Sheets

(51) Int. Cl.
   G09B 21/00    (2006.01)
   G06K 9/00     (2006.01)
   H04N 5/232    (2006.01)
   G08B 3/10     (2006.01)
   G08B 6/00     (2006.01)
   G06F 17/27    (2006.01)
   G06K 9/74     (2006.01)
   G10L 13/04    (2013.01)
   G06F 3/16     (2006.01)
   G06F 3/01     (2006.01)
   H04N 5/225    (2006.01)
   G02C 11/00    (2006.01)

(52) U.S. Cl.
   CPC ............... *G08B 6/00* (2013.01); *G09B 21/00* (2013.01); *G09B 21/001* (2013.01); *G09B 21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G02C 11/10* (2013.01)

(56) References Cited

U.S. PATENT DOCUMENTS

| | | |
|---|---|---|
| 2006/0017810 A1 | 1/2006 | Kurzweil et al. |
| 2012/0212593 A1 | 8/2012 | Na'aman et al. |
| 2012/0330646 A1 | 12/2012 | Andrade et al. |
| 2013/0035742 A1 | 2/2013 | Talbot |
| 2013/0107026 A1* | 5/2013 | Kim ............................... 348/77 |
| 2013/0169536 A1 | 7/2013 | Wexler et al. |
| 2013/0250078 A1* | 9/2013 | Levy ............................... 348/62 |
| 2013/0271584 A1 | 10/2013 | Wexler et al. |

OTHER PUBLICATIONS

Balduzzi, et al., "Low-cost face biometry for visually impaired users," *2010 IEEE Workshop on Biometric Measurements and Systems for Security and Medical Applications* (*BIOMS*), Sep. 9, 2010, pp. 45-52, IEEE, Piscataway, NJ, USA.

European Patent Office, PCT International Search Report, International Application No. PCT/IB2014/000912, Aug. 13, 2014, 4 pages.

European Patent Office, Written Opinion of the International Searching Authority, International Application No. PCT/IB2014/000912, Aug. 13, 2014, 4 pages.

Ivanchenko et al., "Real-Time Walk Light Detection with a Mobile Phone," *Computers Helping People with Special Needs*, Lecture Notes in Computer Science vol. 6180, Jul. 14, 2010, pp. 229-234, Springer Berlin, Berlin, Germany.

Shen et al., "Towards a Real-Time System for Finding and Reading Signs for Visually Impaired Users," *Computers Helping People with Special Needs*, Lecture Notes in Computer Science vol. 7383, Jul. 11, 2012, pp. 41-47, Springer Berlin, Berlin, Germany.

* cited by examiner

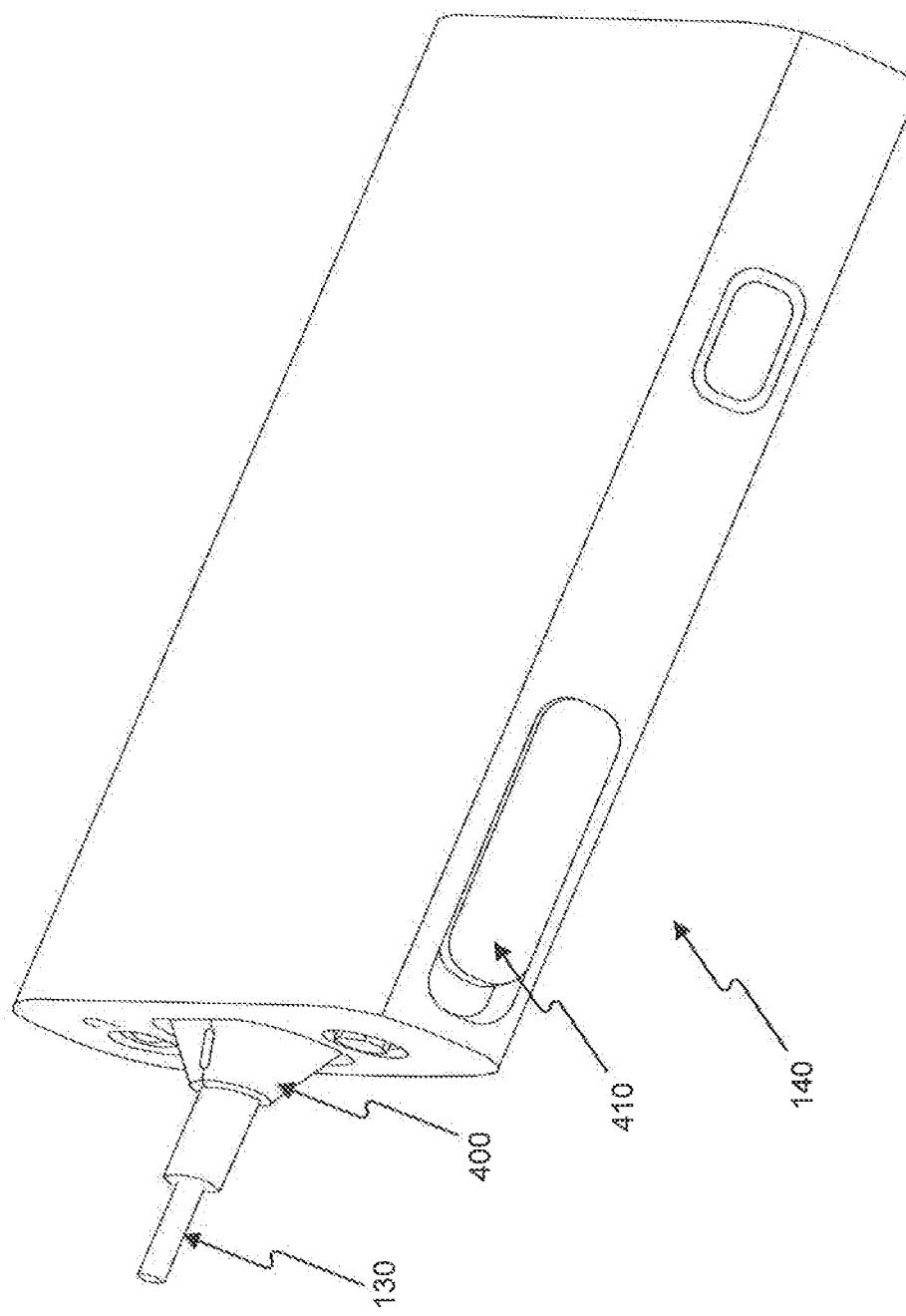

APPARATUS AND METHOD FOR HIERARCHICAL OBJECT IDENTIFICATION USING A CAMERA ON GLASSES

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus is provided for providing environmental information to a visually-impaired user. The apparatus may comprise a portable image sensor configured to be worn by the visually-impaired user and to capture real time image data from an environment of the visually-impaired user, and at least one portable processor device. The portable processor device may be configured to receive the image data and identify a hand-related trigger in the image data. Further, upon identifying the hand-related trigger, the portable processor device may be configured to execute a first search in the image data to identify at least a first object from a first category of objects. Also, after initiating the first search, the portable processor device may be configured to execute a second search in at least one of the image data or results from the first search to identify at least a second object from a second category of objects, differing from the first category of objects. The portable processor device may be further configured to cause audible feedback to be output to the visually-impaired user, wherein the audible feedback includes information related to at least one of the first and second objects identified in the image data.

In accordance with another disclosed embodiment, an apparatus is provided for providing environmental information to a user. The apparatus may comprise an image sensor configured to be worn by user and to capture real time image data from an environment of the user, and at least one processor device. The processor device may be configured to receive the image data from the image sensor. Further, the processor device may be configured to execute a first search in the image data in an attempt to identify a first object from a first category of objects. Also, the processor device may be configured to execute a second search in the image data in an attempt to identify a second object from a second category of objects, differing from the first category of objects. The processor device may be further configured to execute a third search in the image data in an attempt to identify a third object from a third category of objects, differing from the first category of objects and the second category of objects. Additionally, the processor device may be configured to execute a fourth search in the image data in an attempt to identify a fourth object from a fourth category of objects, differing from the first category of objects, the second category of objects, and the third category of objects. The processor device may be configured to execute an action associated with at least one of the first object, the second object, the third object, and the fourth object identified in the image data. Further, the processor device may be configured to cause audible feedback to be output, wherein the audible feedback includes information related to an identified object.

In accordance with yet another embodiment, a method is provided for providing environmental information to a visually-impaired user. The method comprises identifying a hand-related trigger in the image data. Further, upon identifying the hand-related trigger, the method includes executing a first search in the image data in an attempt to identify at least one object from a first category of objects. Also, after initiating the first search, the method comprises executing a second search in the image data in an attempt to identify at least one object from a second category of objects, differing from the first category of objects. The method further includes outputting audible feedback to the visually-impaired user, wherein the audible feedback includes information related to an object identified in the image data.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 4A is a schematic illustration of an example of a processing unit from a first viewpoint;

DETAILED DESCRIPTION

Figure 1:
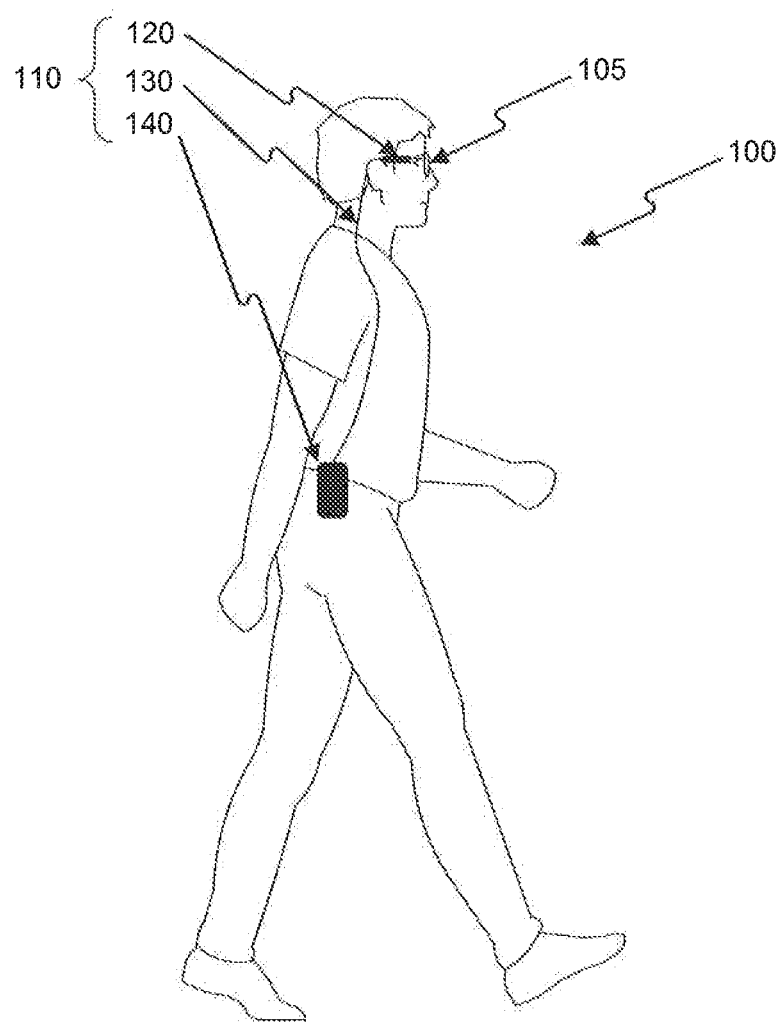
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
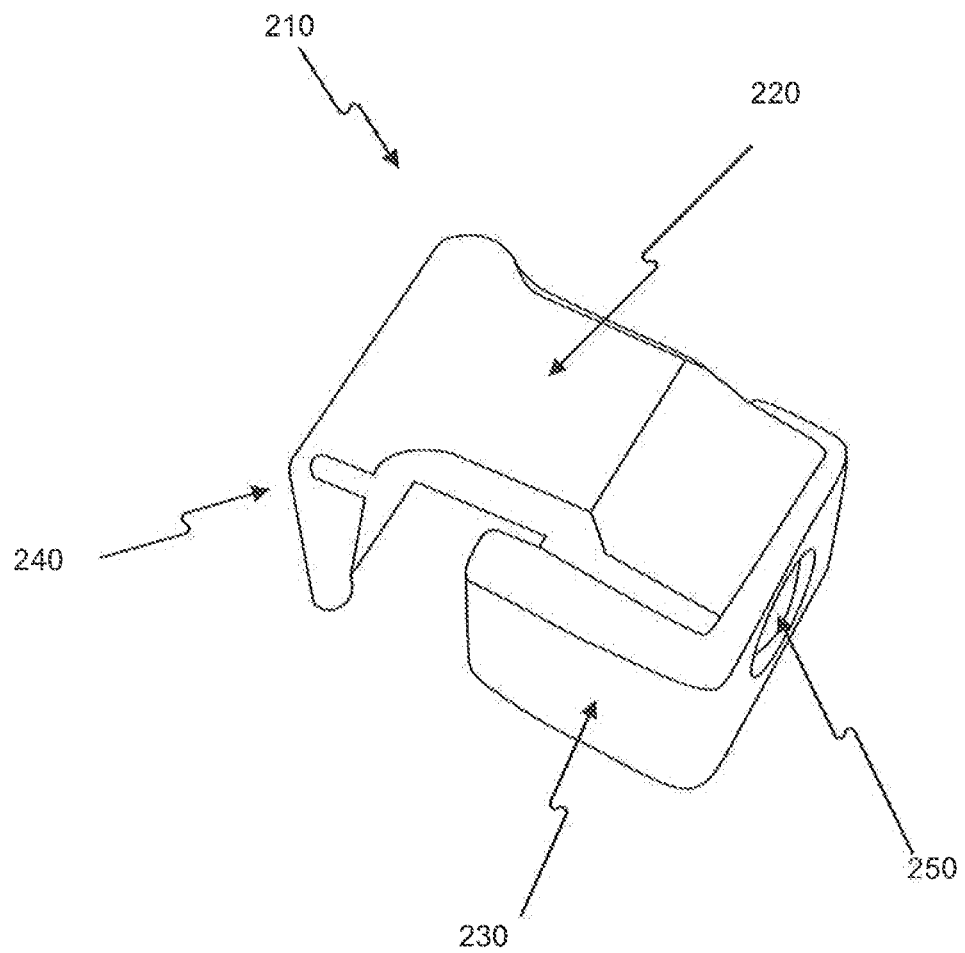
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
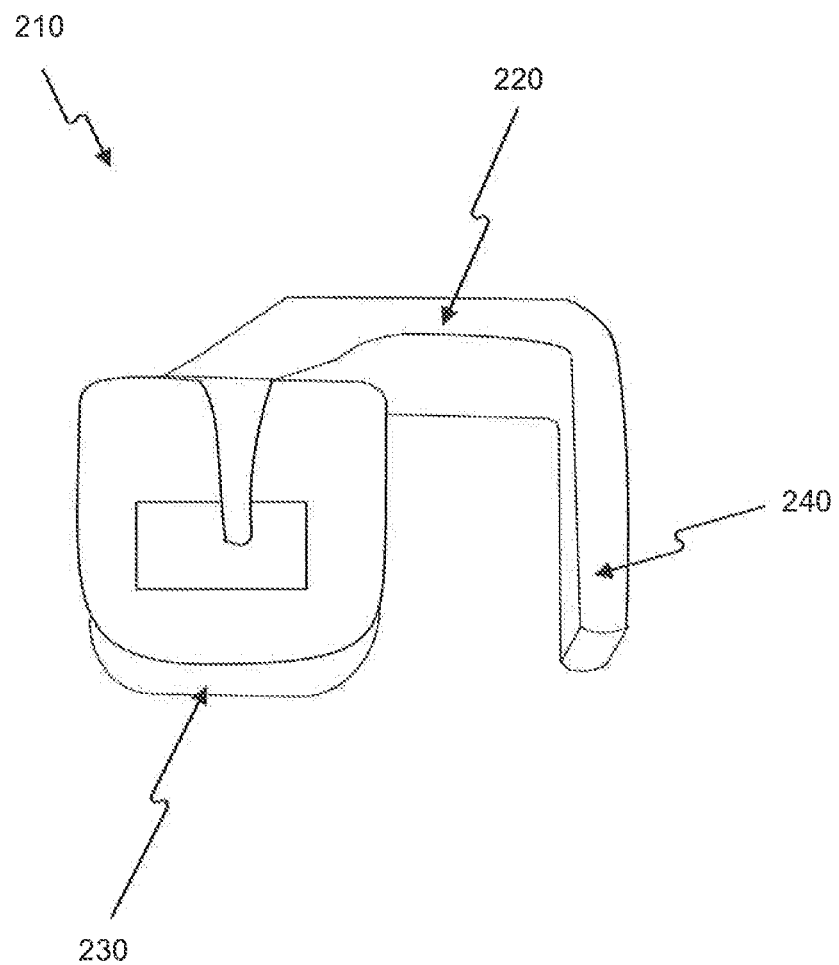
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
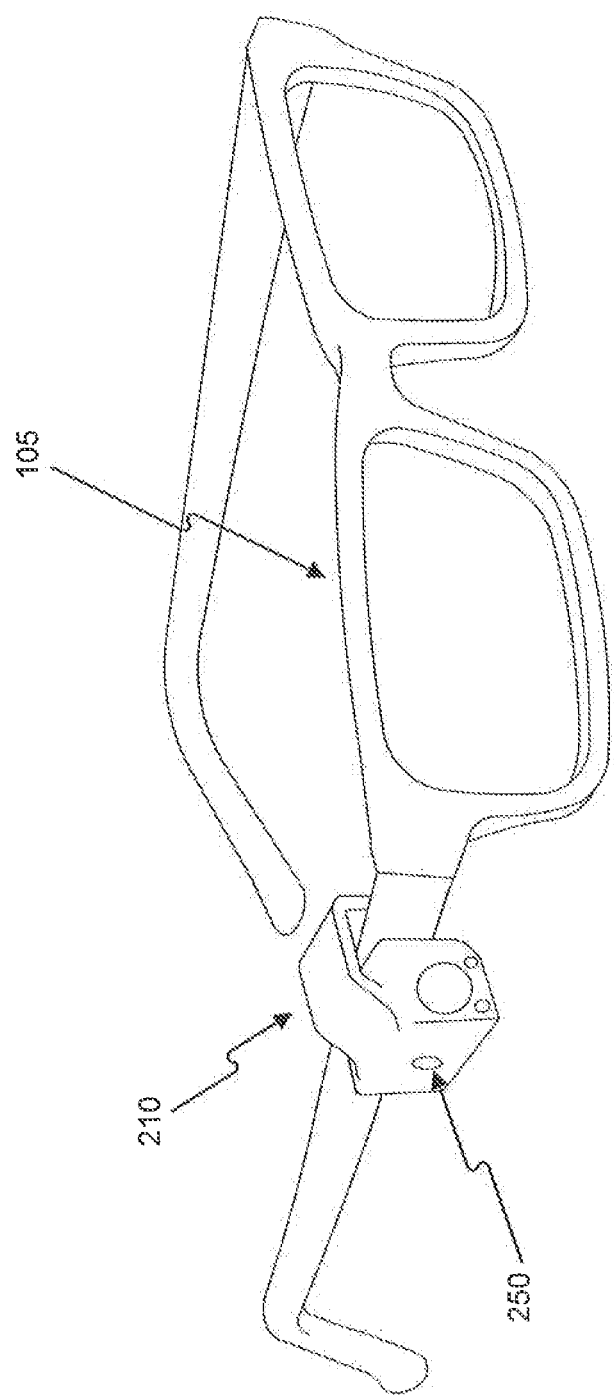
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
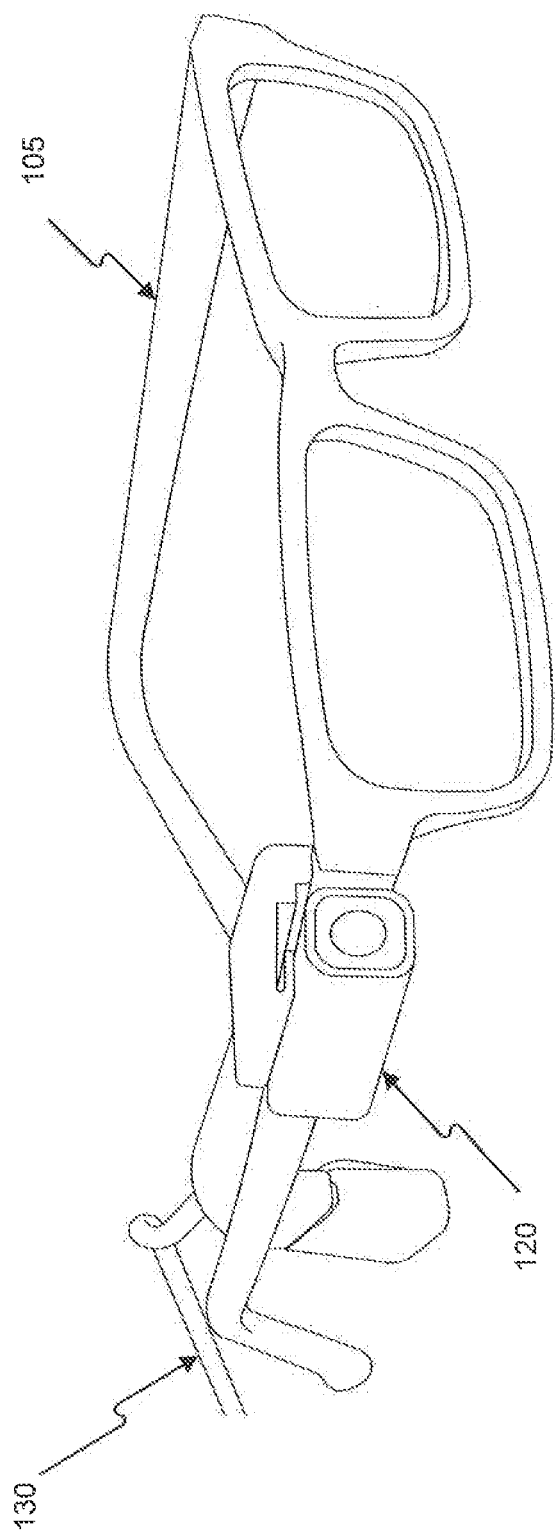
FIG. 2D is a schematic illustration of a sensory unit attached to the support that is mounted on the pair of glasses shown in FIG. 20.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
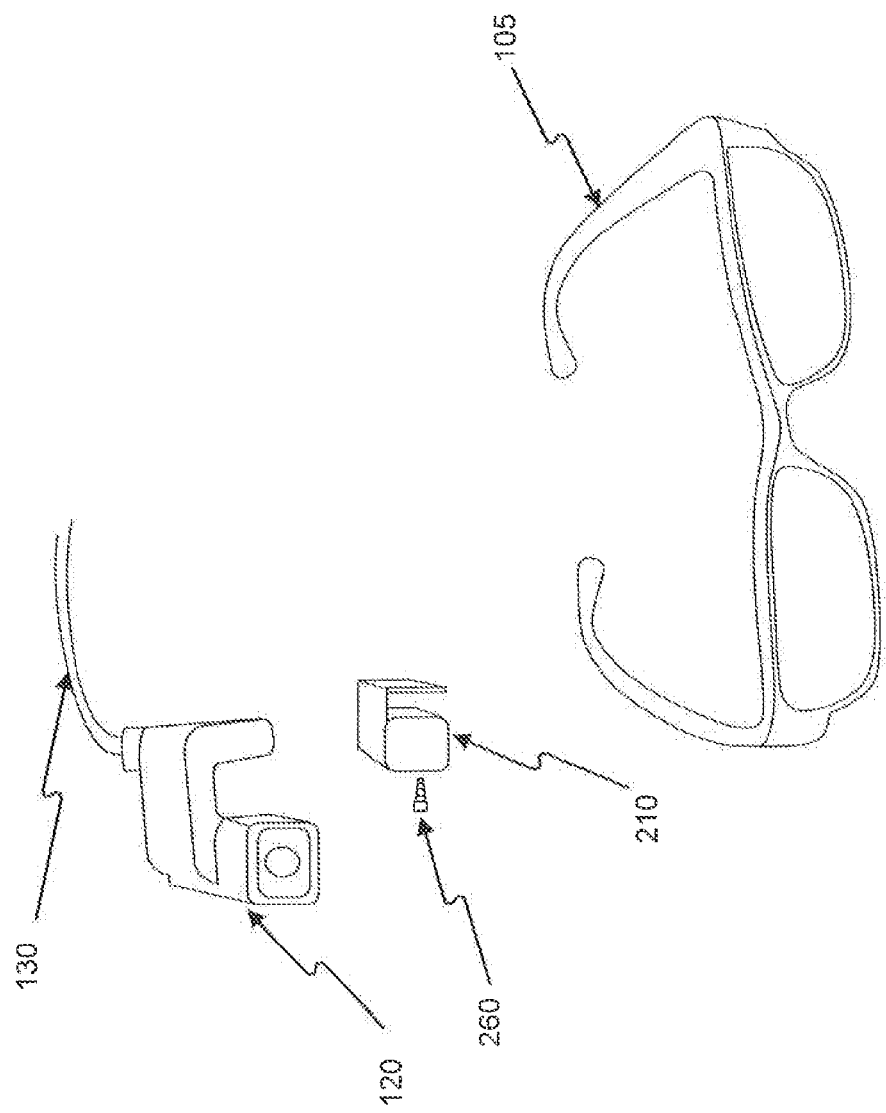
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
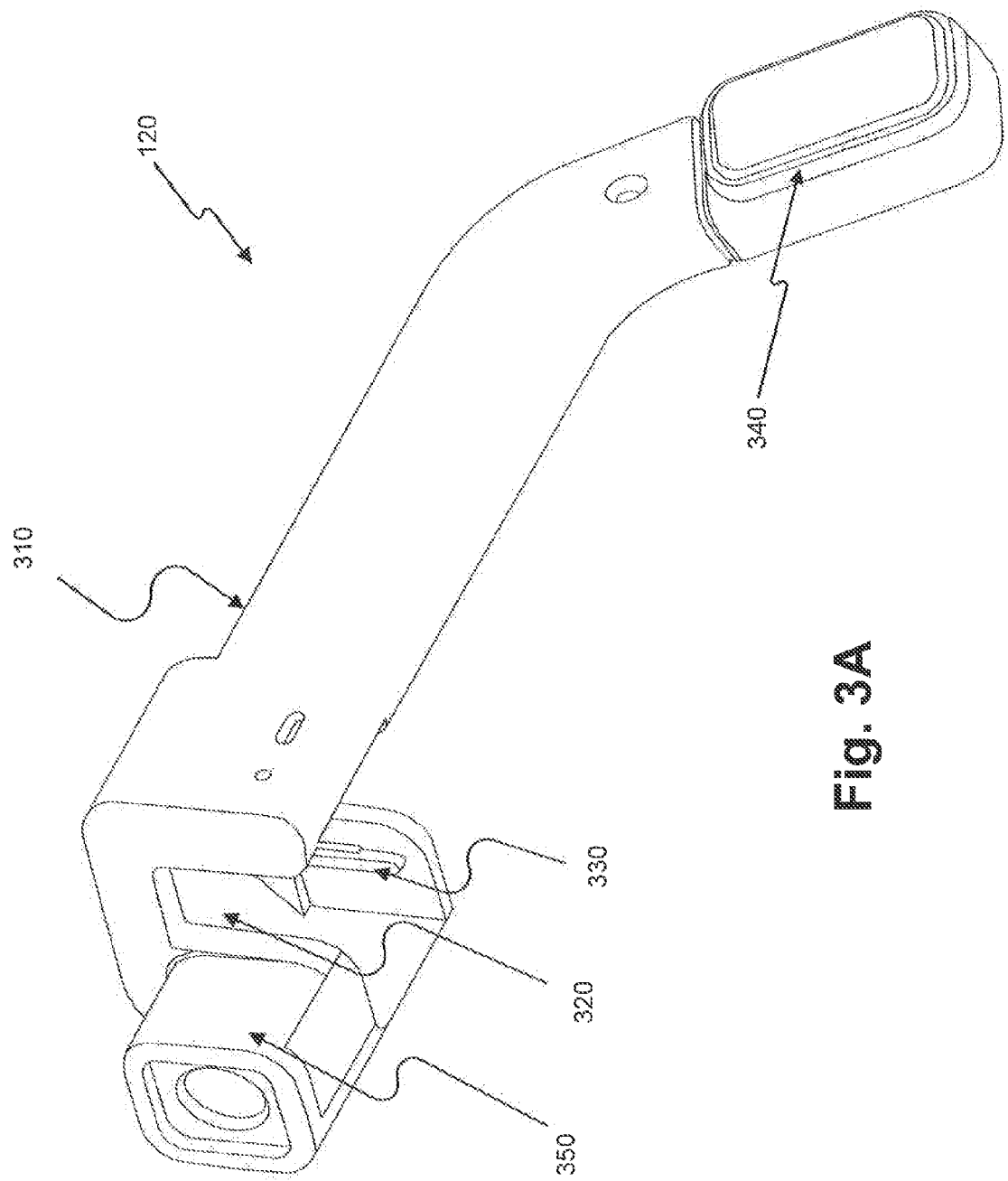
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
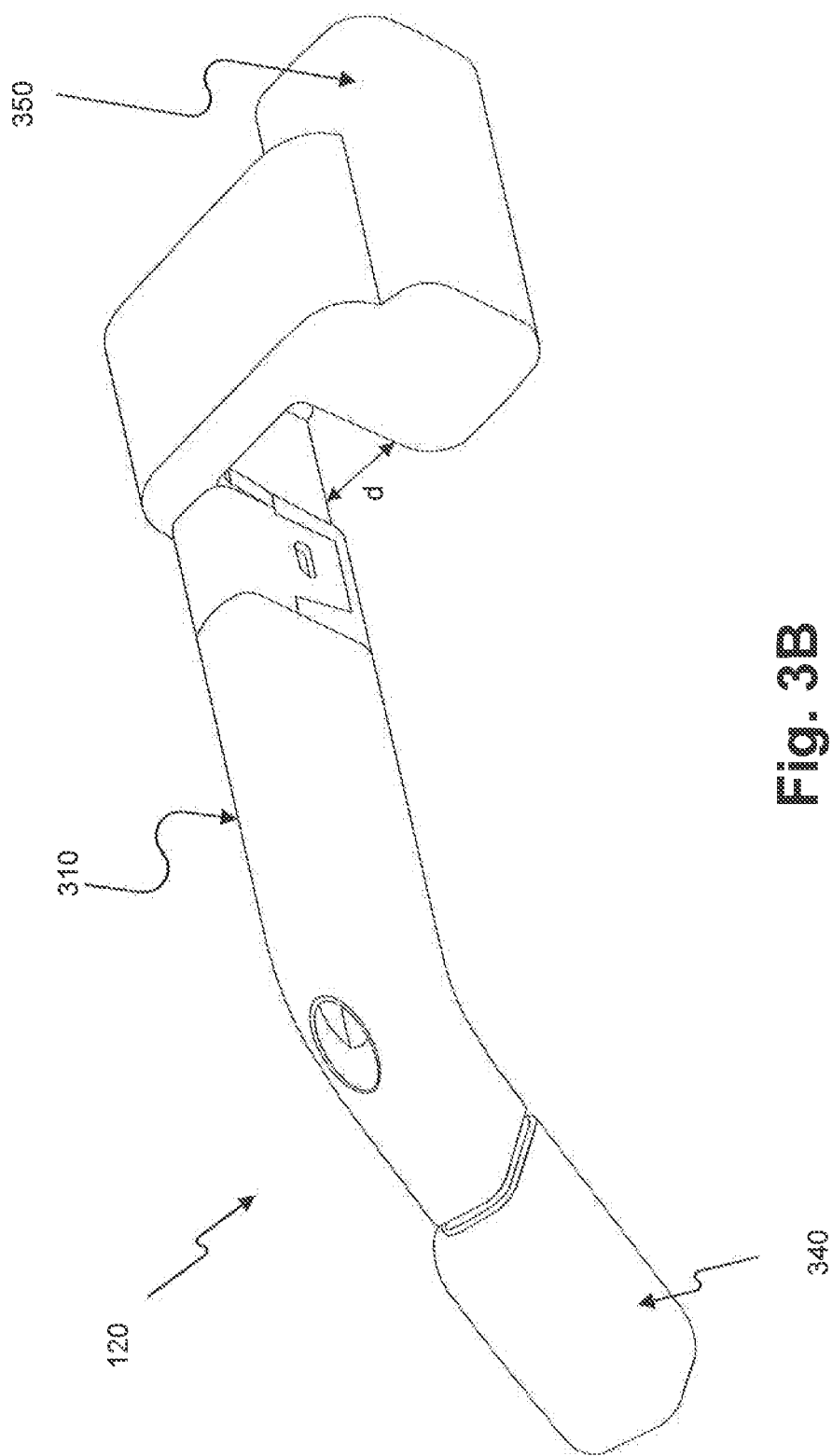
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
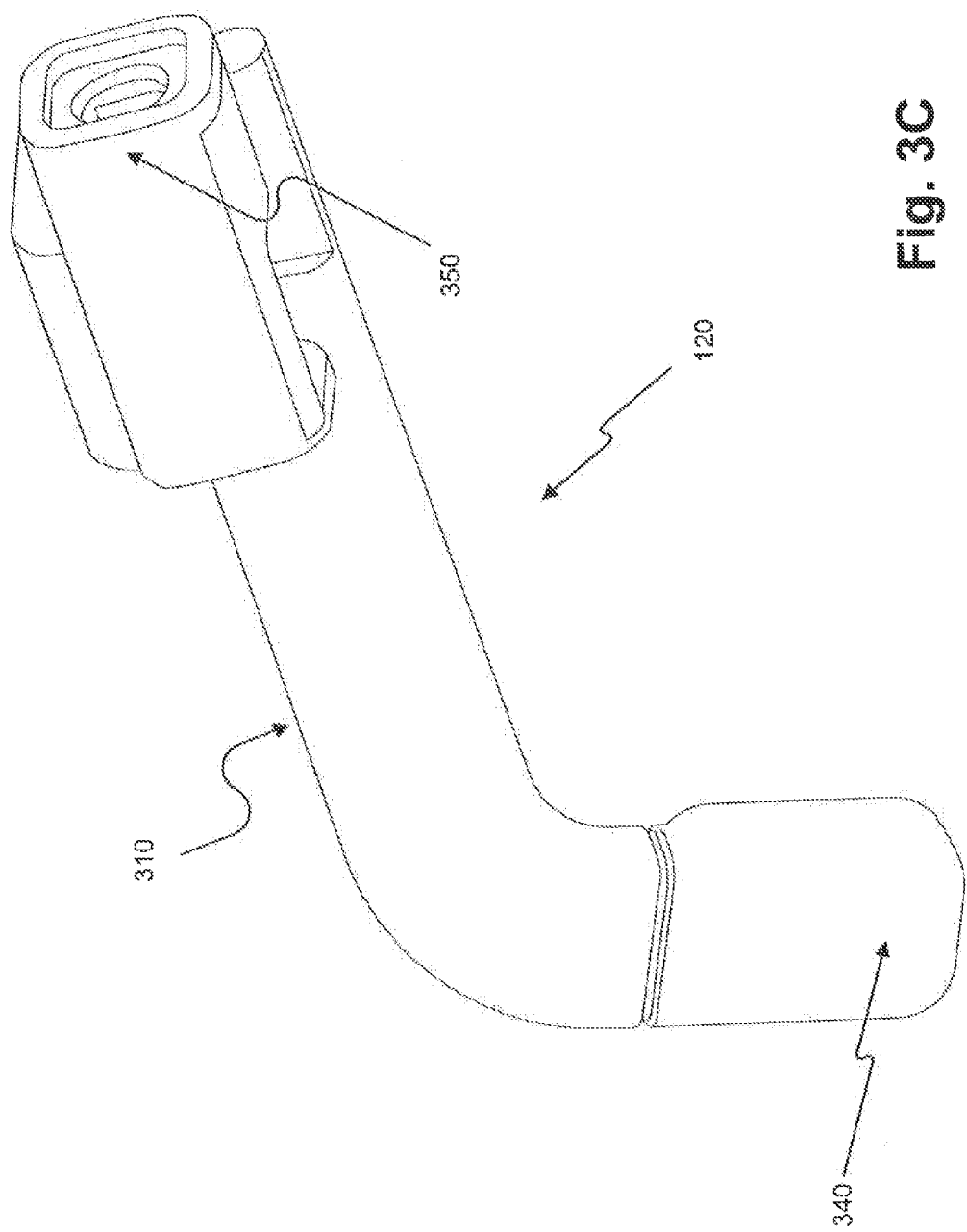
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3O is from a side orientation of sensory unit 120 and shows the side of the U-shaped element that includes image sensor 350.

Figure 3D:
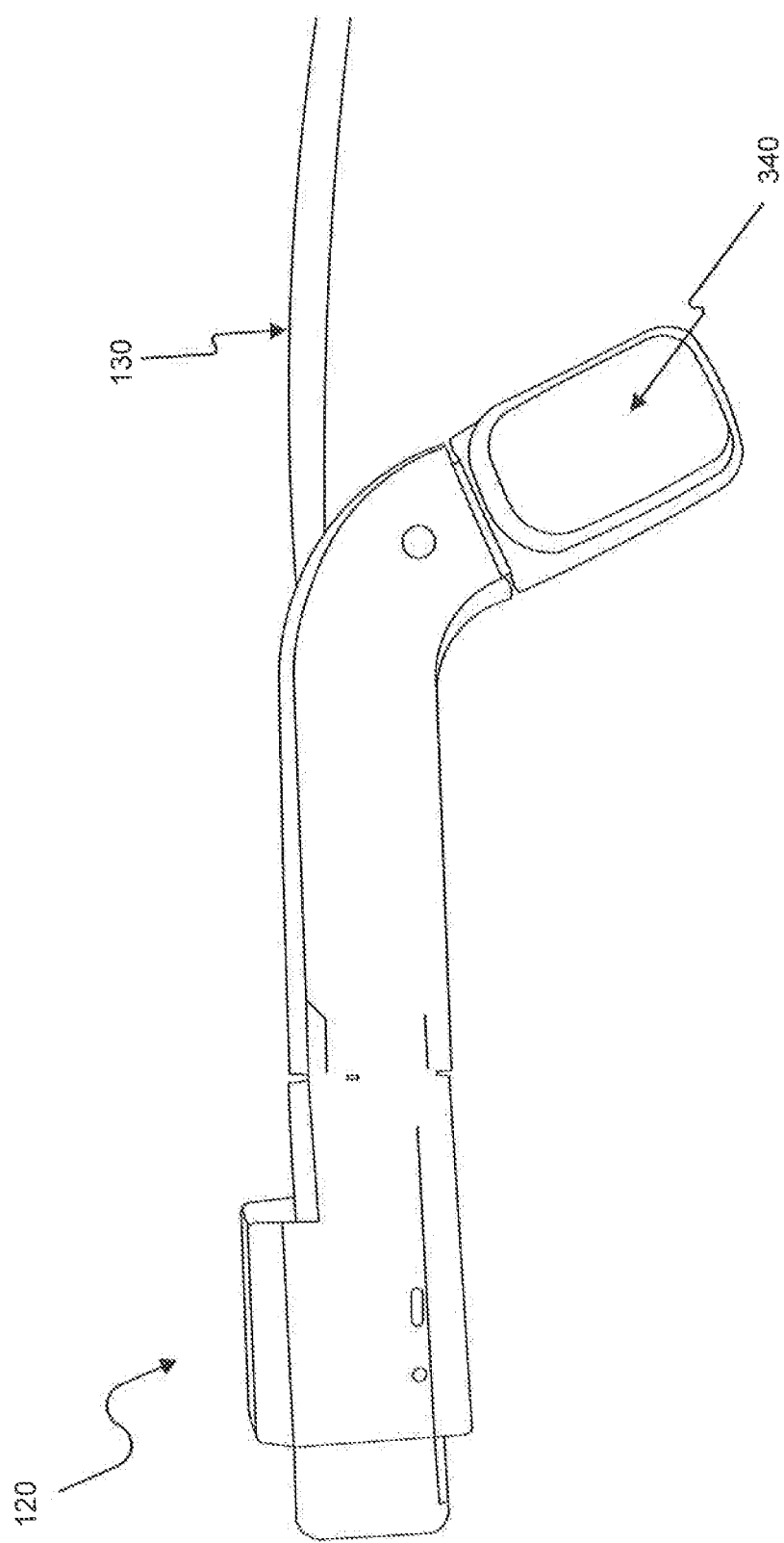
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
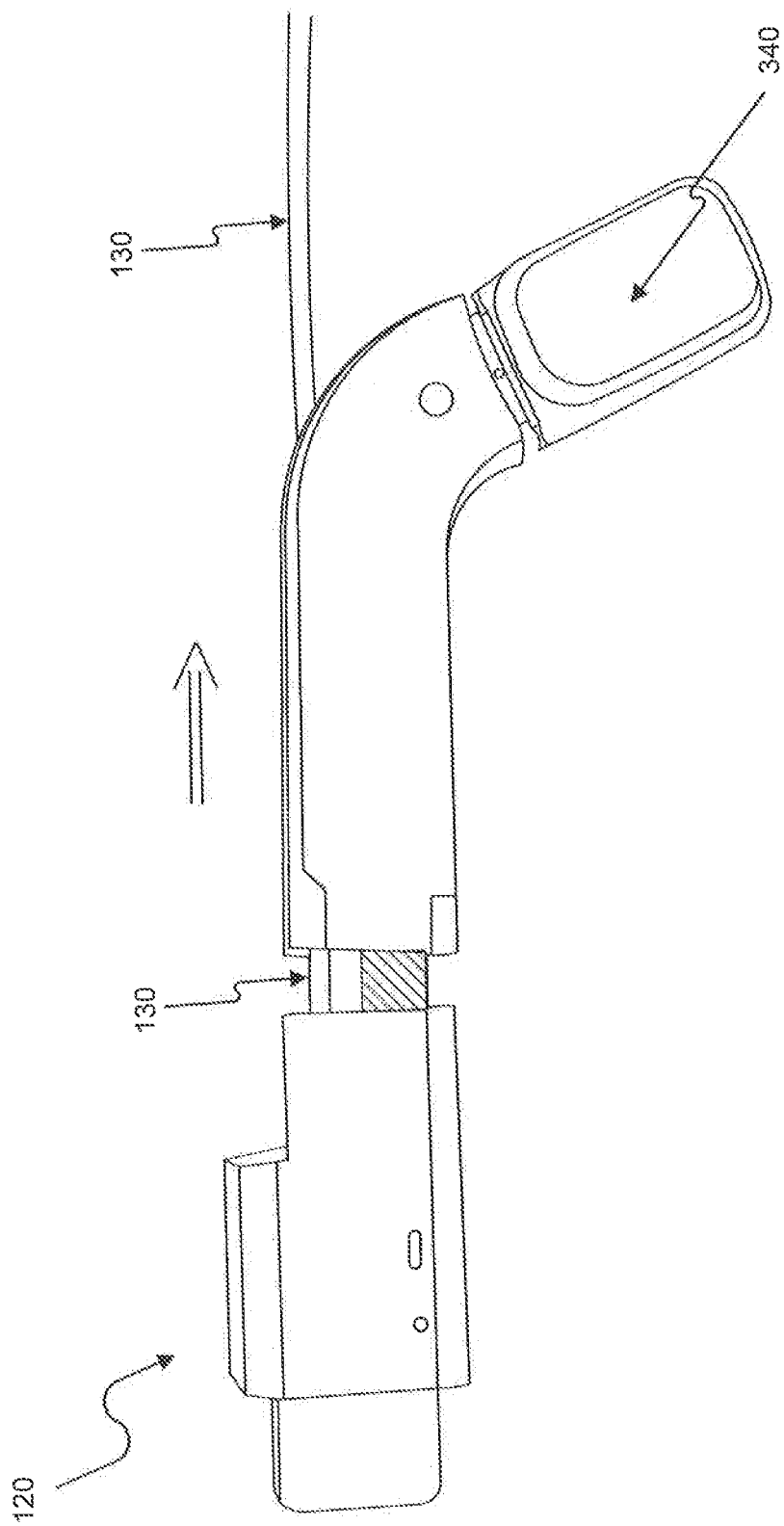
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
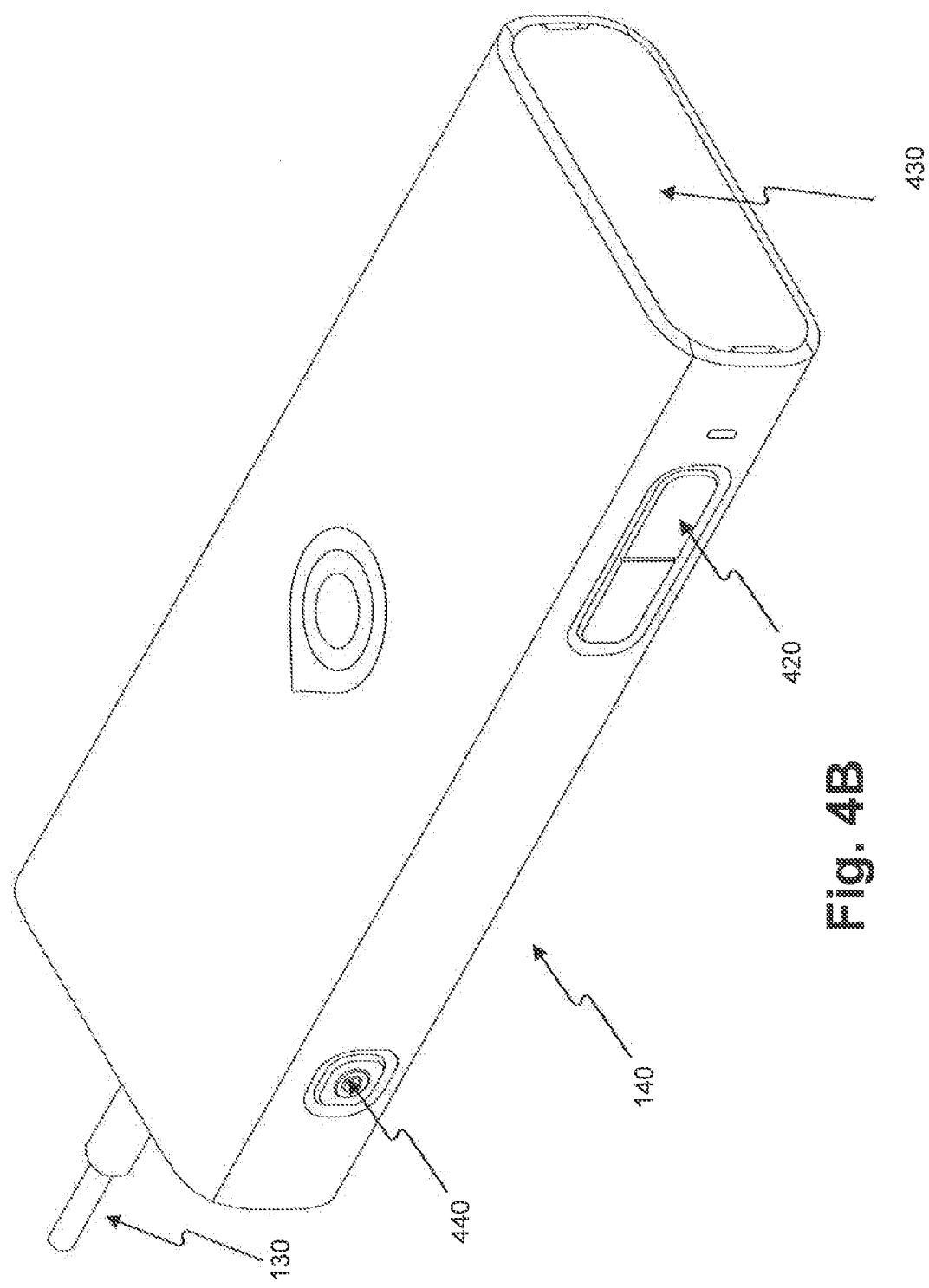
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
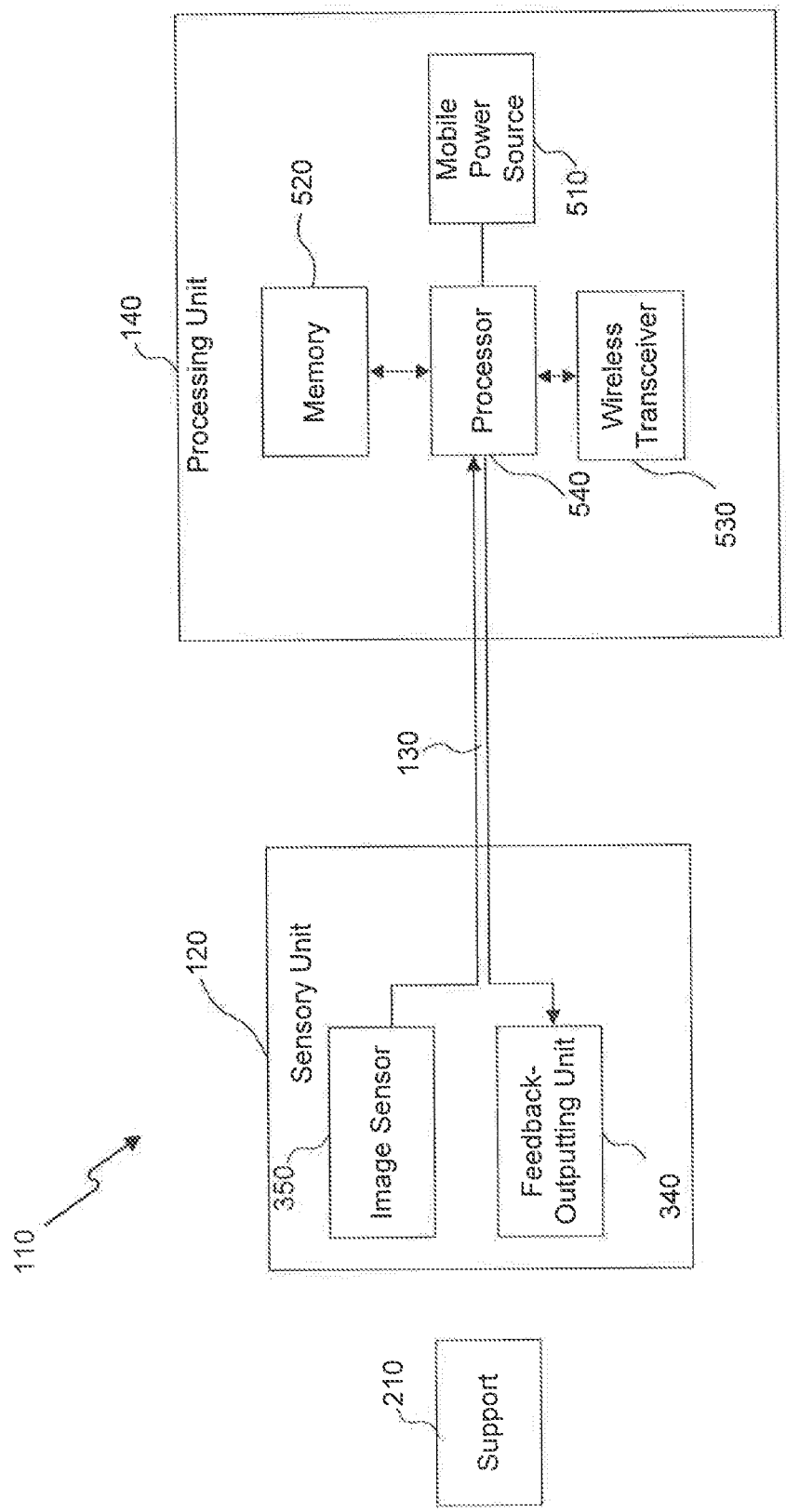
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into the processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
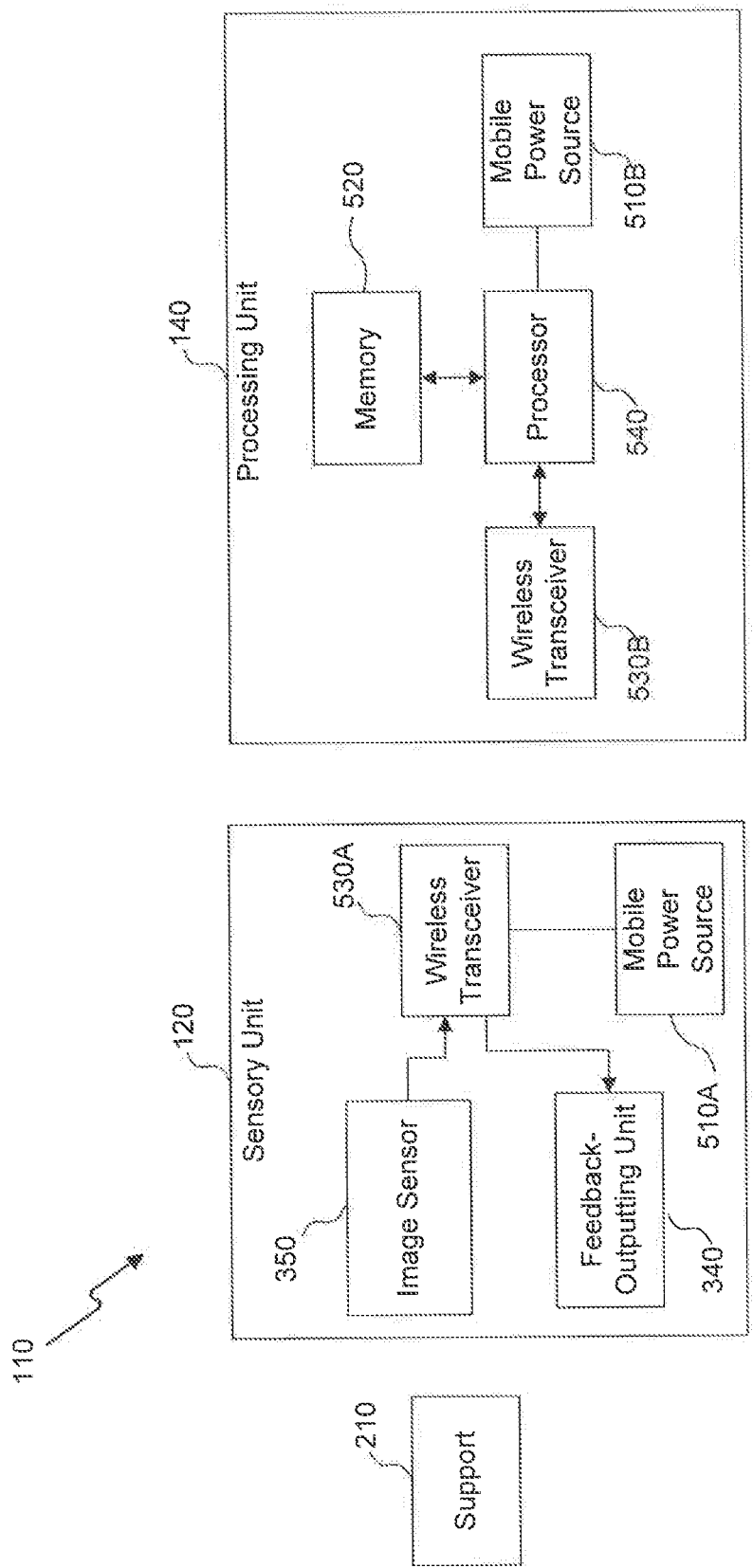
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
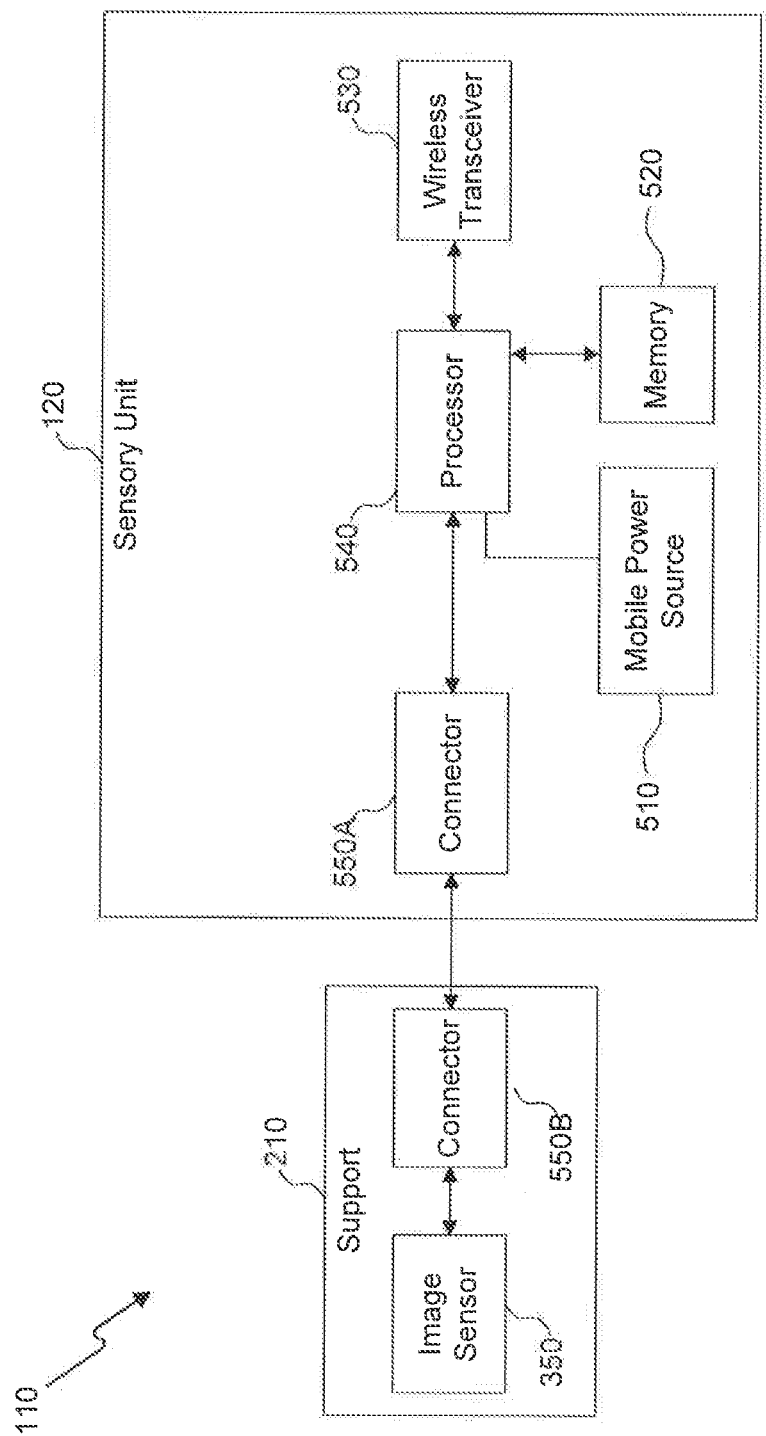
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
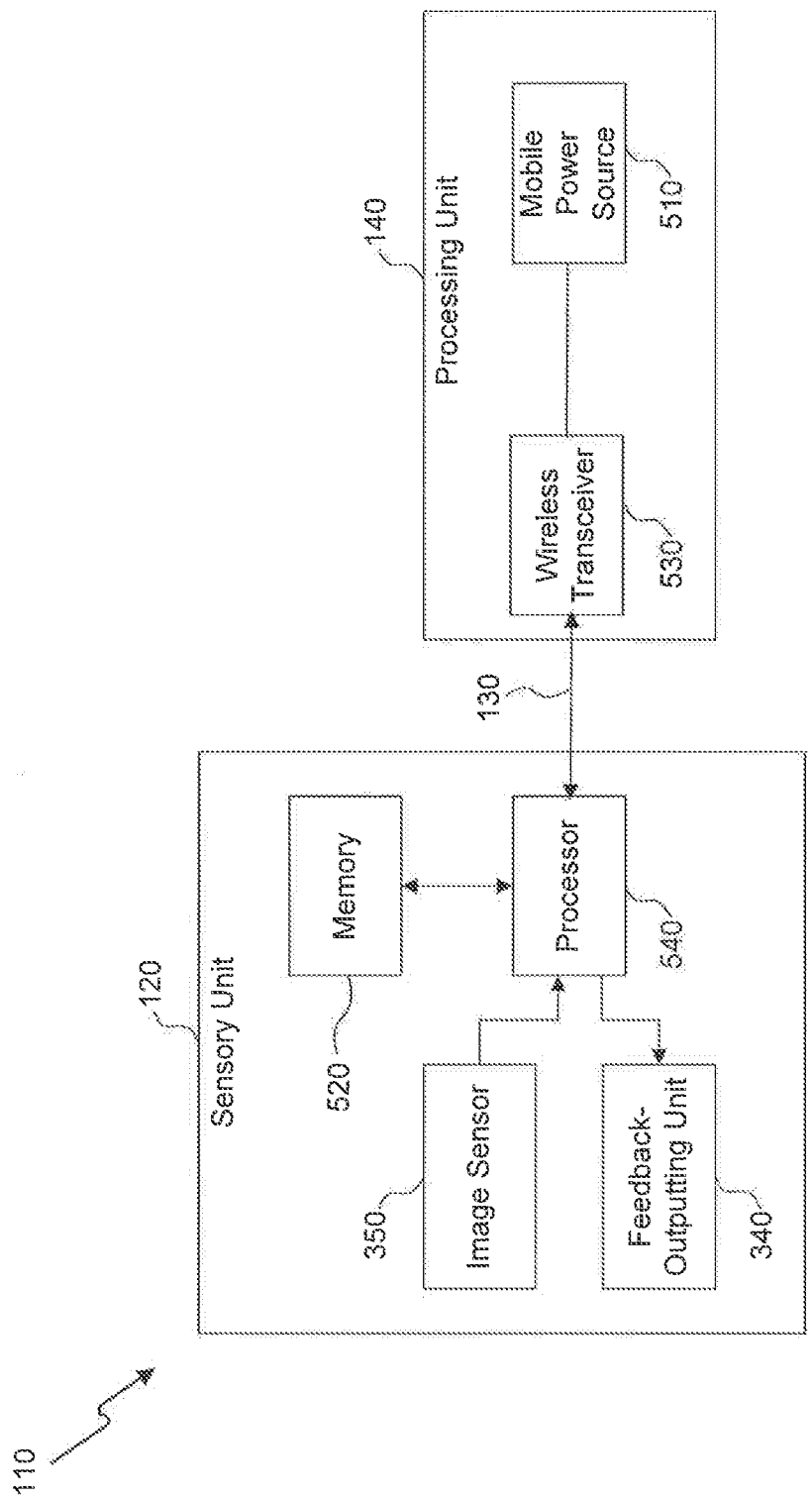
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides a method for providing user 100, who may be visually impaired, with information about one or more objects or situations detected within the field of view of apparatus 110. Apparatus 110 may be configured to place detected objects or situations into categories, and may be operable to perform a hierarchical search of databases that contain information about objects and situations that user 100 may encounter. The hierarchical search capability may provide user 100 with more nuanced information about their surroundings and may enable faster, more topical reactions to environmental stimuli.

Figure 6:
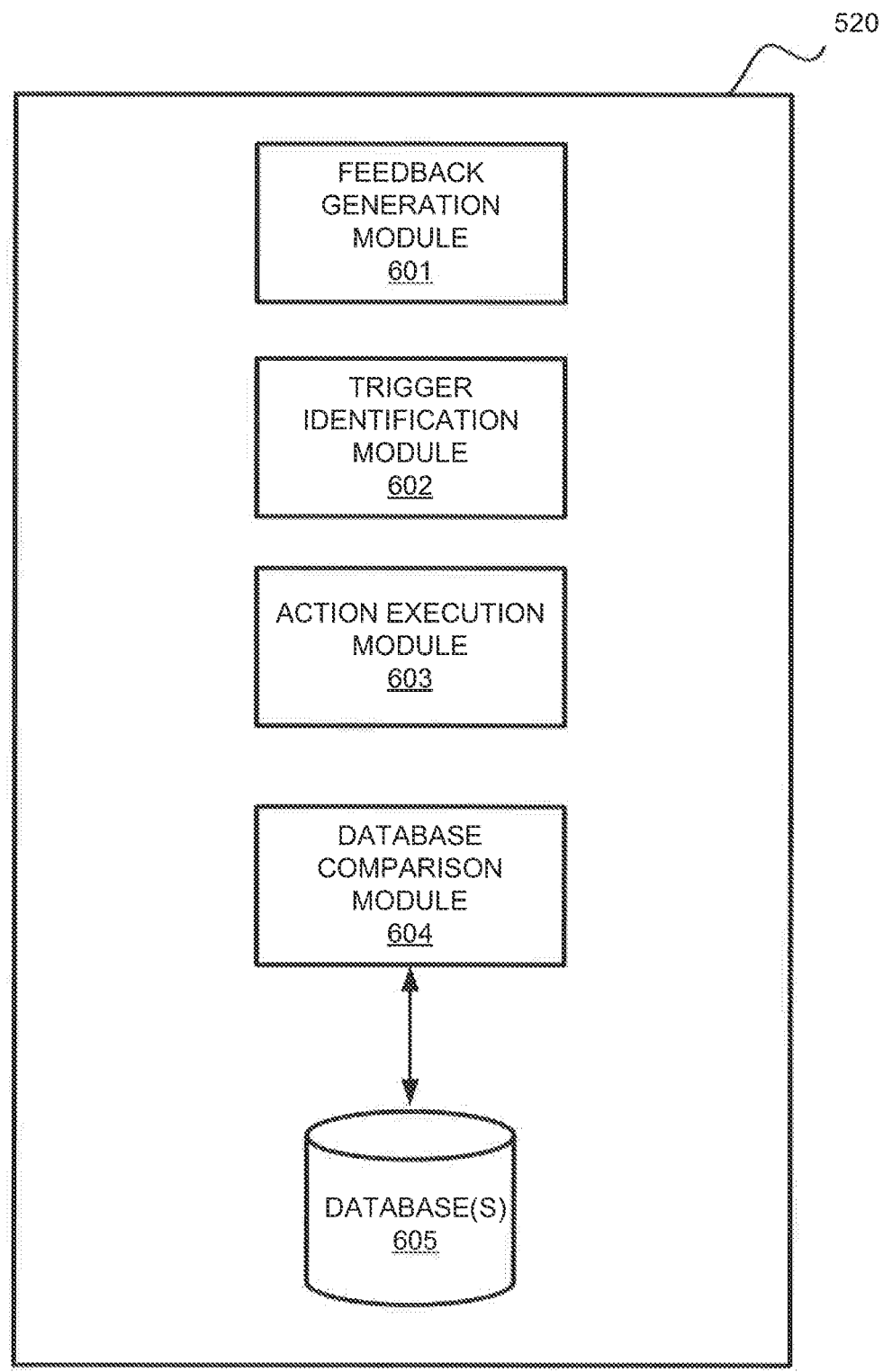
FIG. 6 is a block diagram illustrating an example of a memory contained within an apparatus for aiding persons who have low vision.

FIG. 6 is a block diagram illustrating memory 520 associated with apparatus 110 according to one embodiment. In the example shown in FIG. 6, memory 520 comprises a feedback generation module 601, a trigger identification module 602, an action execution module 603, a database comparison module 604, and one or more databases 605.

Feedback generation module 601 may provide functionality for apparatus 110 to generate and transmit information to user 100 in response to a query. Processor 540 may execute feedback generation module 601 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 601 may generate audible feedback to user 100. In other embodiments, the feedback may be tactile in nature, such as a vibration.

Trigger identification module 602 may provide functionality for apparatus 110 to identify in real-time audible or visual triggers that may precipitate a change in the operational status of apparatus 110. As used in this disclosure, a "trigger" may include, for example, the appearance of user 100's hand within the field of view of apparatus 100 while making a pre-defined gesture. Any external stimulus may constitute a trigger. In some embodiments, for example, user 100 may be able to audibly say words that serve as triggers, such as "Show," "When," "What," etc. It is understood that these are non-limiting examples. Trigger identification module 602 may be configured to detect the presence of triggers, then cause processor 540 to execute software instructions that operate apparatus 110 in a manner associated with the trigger.

Action execution module 603 may provide functionality for apparatus 110 to execute various functions in response to stimuli, be they triggers managed by user 100, appearance of objects within the field of view of apparatus 110, or other events occurring while apparatus 110 is in operation. Action execution module 603 may, for example, coordinate the configuration and execution of one or more alternative actions that may be available to apparatus 110 upon positive identification of an object or a particular situation.

Database comparison module 604 may provide functionality for apparatus 110 to compare objects detected in the user environment to objects and/or categories of said objects in a database, such as database(s) 605, to be described in detail below. In some embodiments, database comparison module 604 may derive information from real time image data received from image sensor 350. In other embodiments, other software elements or processors may derive the information and provide it to database comparison module 604. Processor 540 may execute database comparison module 604 to access one or more of the described databases, and compare the information derived from the received real time image data with information in the databases. If the derived information corresponds to information found in one or more of the databases, database comparison module 604 may provide an indication to feedback generation module 601 to that effect as discussed in further detail below in association with FIGS. 9-11.

Database(s) 605 may comprise one or more databases that store information and are accessed and/or managed through memory 520. By way of example, databases 605 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 605 may contain software code or macros that facilitate rapid searching and comparison by database comparison module 604.

Feedback generation module 601, trigger identification module 602, action execution module 603, and database comparison module 604 may be implemented in software, hardware, firmware, a mix of any of those, or the like. For example, if the modules are implemented in software, they may be stored in memory 520, as shown in FIG. 6. Other components of processing unit 140 and/or sensory unit 120 may be configured to perform processes to implement and facilitate operations of the modules. Thus, feedback generation module 601, trigger identification module 602, action execution module 603, and database comparison module 604 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., feedback generation module 601, trigger identification module 602, action execution module 603, and database comparison module 604) may each include dedicated sensors (e.g., IR, image sensors, etc.) and/or dedicated application processing devices to perform the functionality associated with each module.

As used herein, real-time image data may refer to image data captured in real-time or near real-time. For example, trigger identification module 602 may monitor the field-of-view of apparatus 110 to detect inputs while action execution module 603 may determine whether to initiate an action. Accordingly, trigger identification module 602 and action execution module 603 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 7:
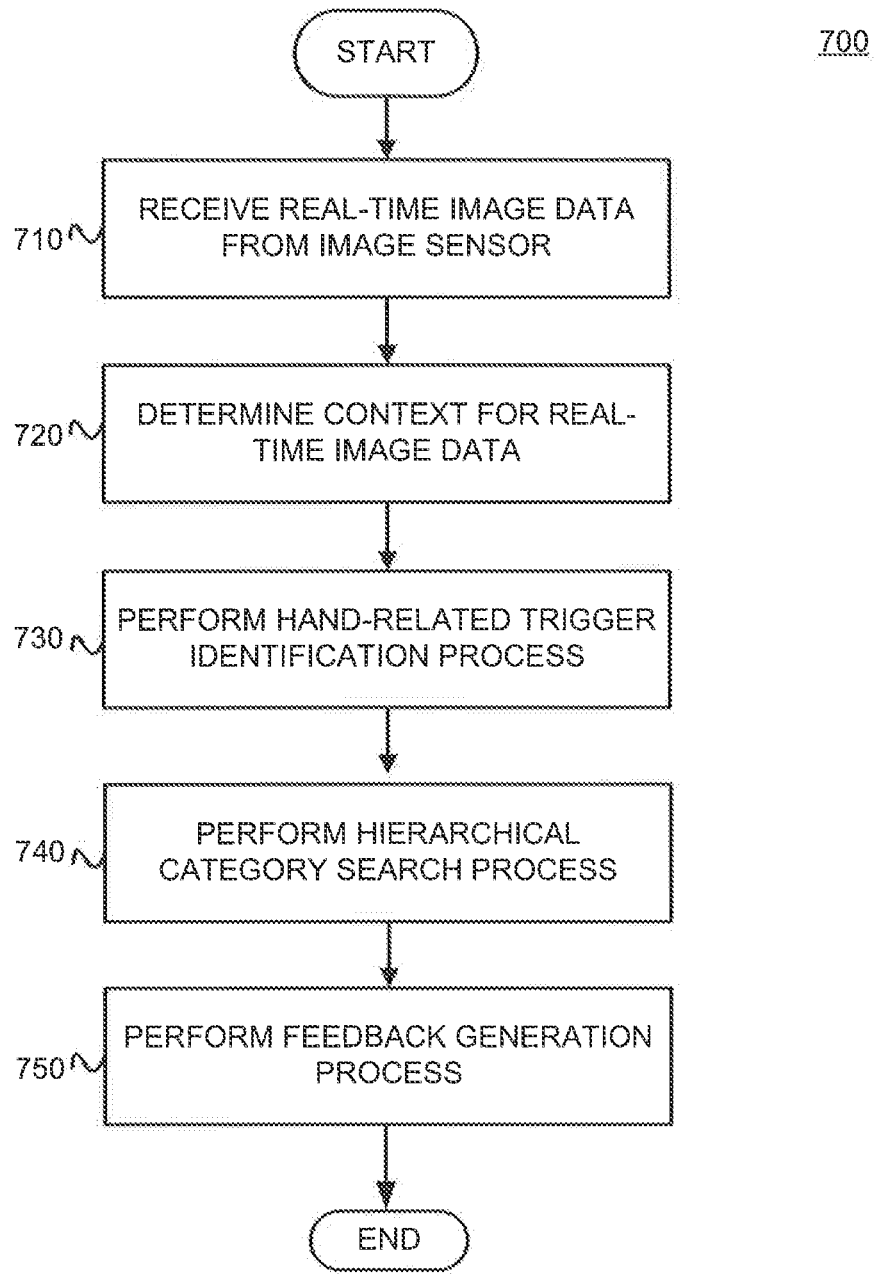
FIG. 7 is an example of a process for providing feedback to a person who has low vision, consistent with disclosed embodiments.

FIG. 7 illustrates an example process 700 for providing feedback to a person who has low vision consistent with certain disclosed embodiments. Process 700, as well as any or all of the individual steps therein, may be performed by various aspects of device 110, such as sensory unit 120, processing unit 140, support 210, or any subcomponents therein. For exemplary purposes, FIG. 7 is described as being performed by processor 540, executing software instructions stored within memory 520.

Processor 540 may receive real-time image data from an image sensor, such as image sensor 350 (Step 710). In other embodiments, processor 540 may receive the image data from an intermediate component associated with sensory unit 120. The intermediate unit may, for example, perform image processing operations on the real-time image data before transmitting it to processor 540. In some embodiments, the real-time image data may be received as a single streaming video file. In other embodiments, the real-time image data may be received as a series of still images. When the image data is received, processor 540 may store the data in memory 520 or database(s) 605.

Processor 540 may determine a context for the received real-time image data based on stored information that facilitates the execution of one or more actions (Step 720). In some embodiments, processor 540 may execute software instructions to process the representations of one or more objects in the real-time image data. In some embodiments, the processing may comprise image processing, such as image rotation, a change in the size of the image, image sharpening, cropping the image, enhancing the focus, etc. It is understood that these are non-limiting examples and that any manner of image processing may be applied to the real-time image data. In other embodiments, the processing may comprise optical character recognition (OCR), when the real-time image data comprises text. In these embodiments, the optical character recognition may facilitate recognition of the visualized text by processor 540, and facilitate formation of a search query for a database containing object information. Processor 540 may further derive or determine any other information contained in the received real-time image data relating to the context of the image, such as date, time, geographical location, etc.

In Step 730 of process 700, processor 540, via trigger identification module 602, may perform a hand-related trigger identification process, such as is described below in connection with FIG. 9. In brief, according to some embodiments, trigger identification module 602 may configure components of apparatus 110, such as image sensor 350 and/or other components of sensory unit 120 and processing unit 140, to operate in a "ready mode" for trigger detection. Trigger identification module 602 may determine if a user's hand is present in the real-time image data. If the user's hand is present, trigger identification module 602 may determine the user hand trigger, if any, that is represented in the real-time image data. Trigger identification module 602 may further determine one or more data categories associated with the determined hand trigger.

Processor 540, via database comparison module 604, may perform a hierarchical search process, such as is described below in connection with FIG. 10 (Step 740). In brief, according to some embodiments, database comparison module 604 may determine objects associated with each data category. Database comparison module 604 may further determine a category with the highest priority based on the determined context for the real-time image data. Processor 540, via database comparison module 604, may search the real-time image data for objects associated with the category. The processor may determine if additional categories are to be searched. If so, database comparison module 604 may determine the category with the next highest priority, and repeat the search process. Once it is determined that no additional categories should be searched, processor 540 may provide information about the identified objects to feedback generation module 601.

Processor 540, via feedback generation module 601, may perform a feedback generation process, such as is described below in connection with FIG. 11 (Step 750). In brief, according to some embodiments, feedback generation module 601 may receive information associated with one or more objects identified in the real-time image data. Feedback generation module 601 may determine audible feedback for output to user 100. Feedback generation module 601 may configure the audible feedback, and then provide the audible feedback to feedback-outputting unit 430 for output to user 100.

Figure 8B:
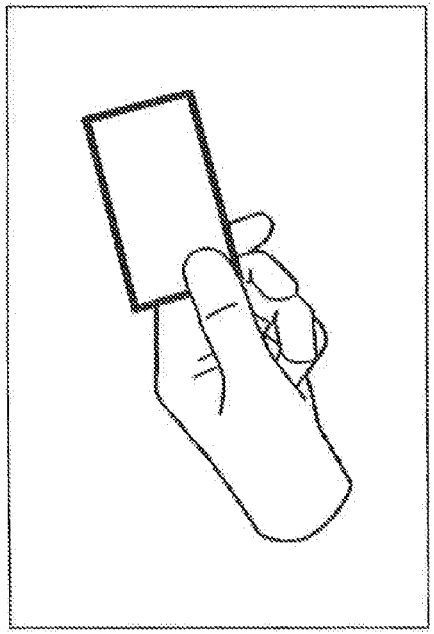
FIG. 8B is an example illustration of a hand-related trigger for an apparatus for aiding persons who have low vision, consistent with disclosed embodiments.
Figure 8D:
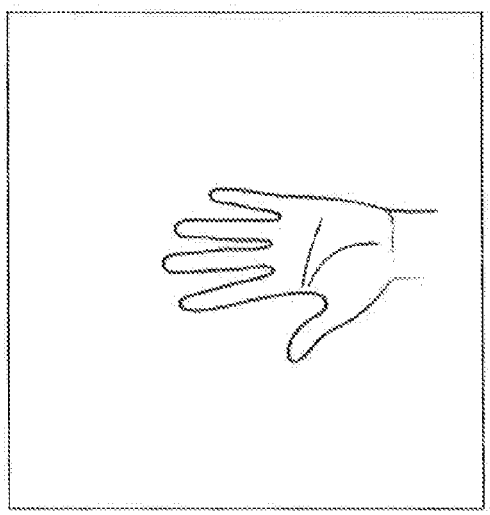
FIG. 8D is an example illustration of a hand-related trigger for an apparatus for aiding persons who have low vision, consistent with disclosed embodiments.
Figure 8A:
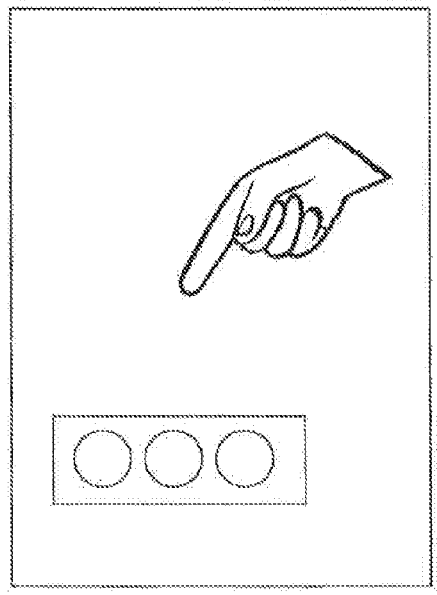
FIG. 8A is an example illustration of a hand-related trigger for an apparatus for aiding persons who have low vision, consistent with disclosed embodiments.

FIGS. 8A-8D illustrate examples of hand-related triggers, consistent with certain disclosed embodiments. FIG. 8A illustrates an example field of view of apparatus 110. In the example of FIG. 8A, a hand of a user, such as user 100, is present within the field of view, and is pointing at an object. In this example, the object is a stoplight, but the object can be any object that may be present in the environment surrounding user 100 while using apparatus 110. In some embodiments, a "pointing" hand trigger as illustrated in FIG. 8A may result in execution of one or more actions relating to the object being pointed at. For example, when user 100 points at a stoplight, as in FIG. 8A, apparatus 110 may detect the action (as will be described below), and audibly announce the status of the stoplight (i.e., "GREEN," "RED," etc.). In other embodiments, a pointing hand trigger may permit apparatus 110 to perform other actions, including, but not limited to, announcing the name of a familiar landscape or a familiar object, announcing route information for a public transportation vehicle, audibly reading text, or audibly recognizing a food item or a pharmaceutical. A pointing hand trigger may be used in disclosed embodiments for any action that provides more information about an object within the field of view of apparatus 110.

FIG. 8B illustrates another example field of view of apparatus 110. In the example of FIG. 8B, a hand of a user, such as user 100, is present within the field of view, and is holding an object. In this example, the object is a piece of paper containing text, but the object can be any object that may be present in the environment surrounding user 100 while using apparatus 110. In some embodiments, a "holding" hand trigger as illustrated in FIG. 8B may result in execution of one or more actions relating to the object being held. For example, when user 100 holds a document or any other item containing text, as in FIG. 8B, apparatus 110 may detect the action (as will be described below), and audibly read the text on the document. In other embodiments, a holding hand trigger may permit apparatus 110 to perform other actions, including, but not limited to, announcing the name of a familiar object that is being held, managing database entries for objects (i.e. removing an item as being recognized, editing audible feedback for an item, etc.), or prompting the user to name an item if the held item is an unfamiliar item, A holding hand trigger may be used in disclosed embodiments for any action that provides more information about an object within the field of view of apparatus 110.

Figure 8C:
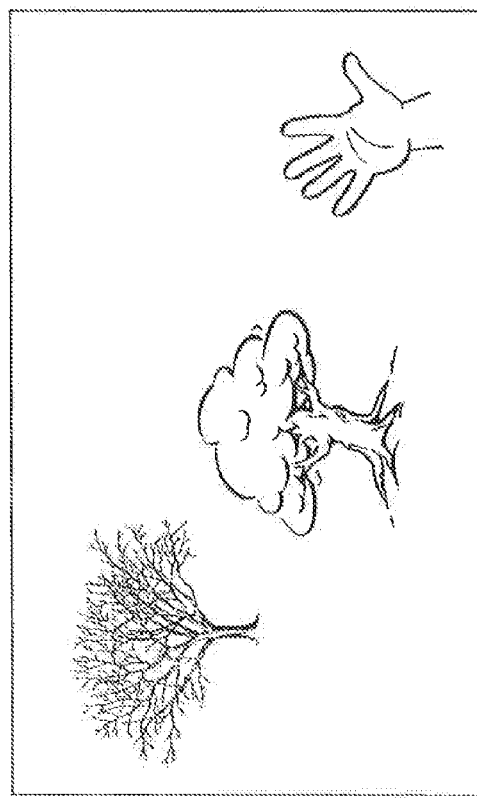
FIG. 8C is an example illustration of a hand-related trigger for an apparatus for aiding persons who have low vision, consistent with disclosed embodiments.

FIG. 8C illustrates another example field of view of apparatus 110. In the example of FIG. 8C, a hand of a user, such as user 100, is present within the field of view, and is waving. In this example, the hand of user 100 is waving in a landscape. In embodiments such as these, a "waving" hand trigger as illustrated in FIG. 8C may result in execution of one or more actions relating to an object or landscape in the field of view when user 100 waves. For example, when user 100 waves at a landscape that is familiar, apparatus 110 may detect elements of the familiar landscape (as will be described below), and audibly identify the location. In other embodiments, a waving hand trigger may permit apparatus 110 to perform other actions, such as prompting the user to identify an unfamiliar landscape when the user waves in an area that is not identifiable by apparatus 110. In some embodiments, waving hand triggers may be associated with pre-programmed landscapes, and landmarks from the landscapes may be stored in memory 520 or database(s) 605. In these embodiments, for example, user 100 may be able to participate in a guided tour of a tourist attraction. In other embodiments, apparatus 110 may be configured to learn landscapes over time by prompting user 100 for information. A waving hand trigger may be used in disclosed embodiments for any action that provides more information about an object within the field of view of apparatus 110.

FIG. 8D illustrates another example field of view of apparatus 110. In the example of FIG. 8D, a hand of a user, such as user 100, is present within the field of view, and is outstretched in a "stop" gesture. In embodiments such as these, a "stop" hand trigger as illustrated in FIG. 8D may result in execution of one or more actions relating to an object or landscape in the field of view when user 100 presents their hand in this manner. For example, when user 100 presents a stop hand trigger during any ongoing operation or action associated with apparatus 110, the apparatus may be configured to immediately terminate the ongoing operation. In other embodiments, the stop hand trigger may serve as a "reset" for apparatus 110, or may be configured to help present user 100 with information about the status of the apparatus.

Figure 9:
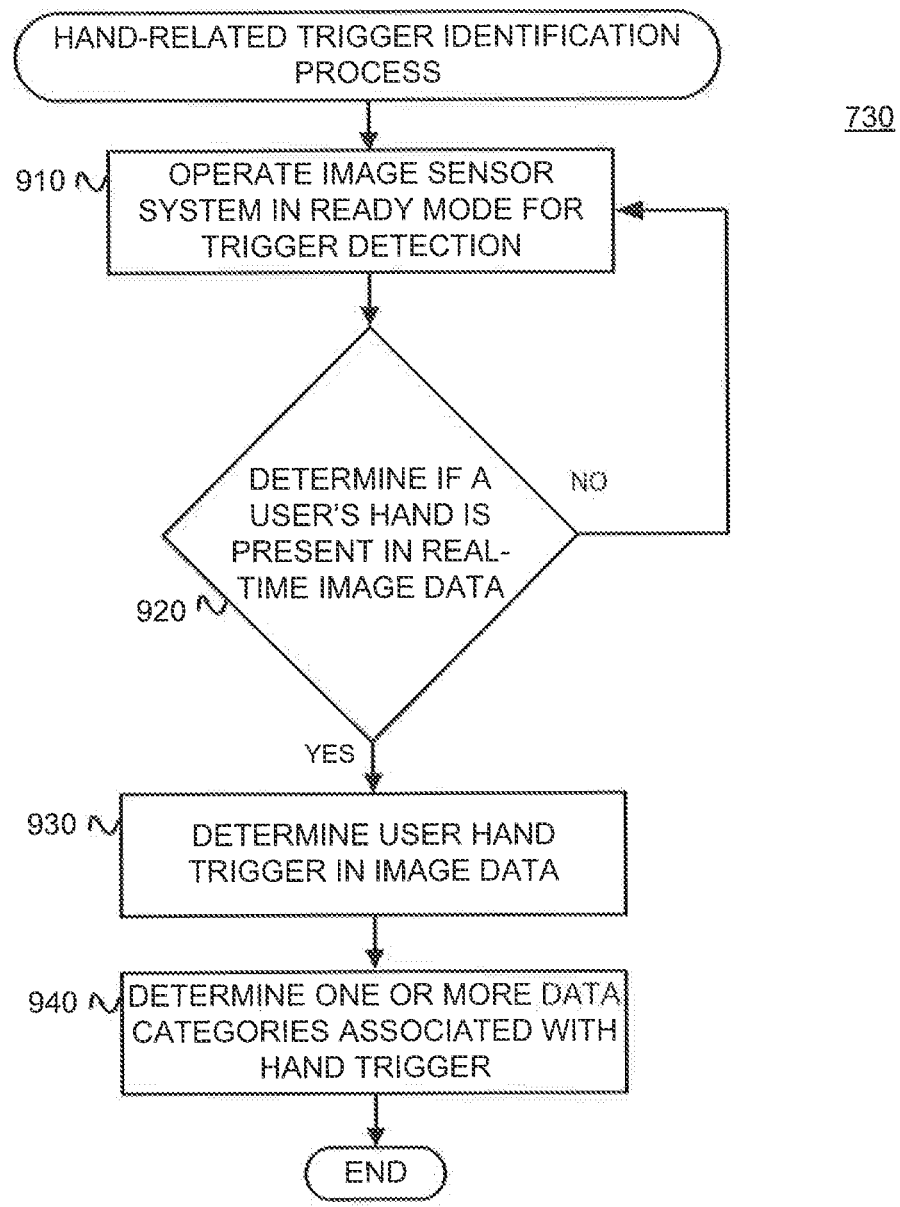
FIG. 9 is an example of a hand-related trigger identification process, consistent with disclosed embodiments.

FIG. 9 illustrates an example of a hand-related trigger identification process, such as that described above in association with Step 730 of process 700 consistent with certain disclosed embodiments. Process 730, as well as any or all of the individual steps therein, may be performed by various aspects of device 110, such as sensory unit 120, processing unit 140, support 210, or any subcomponents therein. For exemplary purposes, FIG. 9 is described as being performed by processor 540, executing software instructions stored within memory 520.

Processor 540, via trigger identification module 602, may operate image sensor 350 in a normal manner, or "ready mode" while awaiting trigger detection (Step 910). In some embodiments, apparatus 110 may be configured to always operate in a ready mode when no operations are active. In other embodiments, user 100 may be able to place apparatus 110 into a ready mode such that a hand trigger may be detected.

While in ready mode, trigger identification module 602 may determine if a user's hand is present in the real-time image data (Step 920). In some embodiments, trigger identification module 602 may be configured to recognize the particular hand of the user 100 that is operating apparatus 110. In these embodiments, apparatus 110 may initially prompt user 100 to mime various hand triggers. Trigger identification module 602 may capture images of the various hand triggers and store them in one or both of memory 520 or database(s) 605 for ready recognition in the future. In alternative embodiments, trigger identification module 602 may not be configured to recognize a particular hand, and may be pre-configured to recognize any hand, similar appendage, or equivalent substitute. In some embodiments, trigger identification module 602 may be configured to recognize the hand of user 100 when it is covered in a glove, mitten, or other covering.

If no hand is detected as present in the real-time image data (Step 920:NO), trigger identification module may configure image sensor 350 to continue to operate in ready mode, waiting for a future trigger. If a hand is determined to be present (Step 920:YES), then trigger identification module 602 may determine if the hand is performing a recognized hand trigger gesture (Step 930). Examples of possible hand triggers are discussed above in association with FIGS. 8A-8D, but additional hand actions may be recognized by trigger identification module 602. Trigger identification module 602 may interact with database comparison module 604 to search a database, such as database 605, for recognized hand triggers.

Trigger identification module 602 may determine one or more data categories associated with the determined hand trigger (Step 940). For example, processor 540 may determine context information associated with the environment surrounding user 100, and may, along with the determined hand trigger, use the information to determine particular categories to search. For example, user 100 may be standing at an intersection desiring to cross the street. Apparatus 110 may detect this scenario as the current setting. Processor 540 may perform a variety of different alternative actions (via action execution module 603) based on a particular hand trigger recognized by trigger identification module 602. For example, one type of hand trigger may signal to trigger identification module 602 that the category to search for is "warning of risks." As will be discussed further below, apparatus 110 may then scan the field of view for objects, then scan the database for matching objects that may represent risks to user 100. In some embodiments, multiple categories may be associated with a given hand trigger in a given context. For example, in the scenario just described, warning of risks may comprise a first category, and a second category may be "scene identification." Numerous combinations of categories are contemplated for various triggers and contexts. For example, in an alternative embodiment, "spatial guidance" may be the first category, and "warning of risks" may be the second category. Categories may be fluid based on current configuration of apparatus 110 at any given time. One skilled in the art may contemplate many possible categories of data and contexts in which they could be invoked or sorted.

Figure 10:
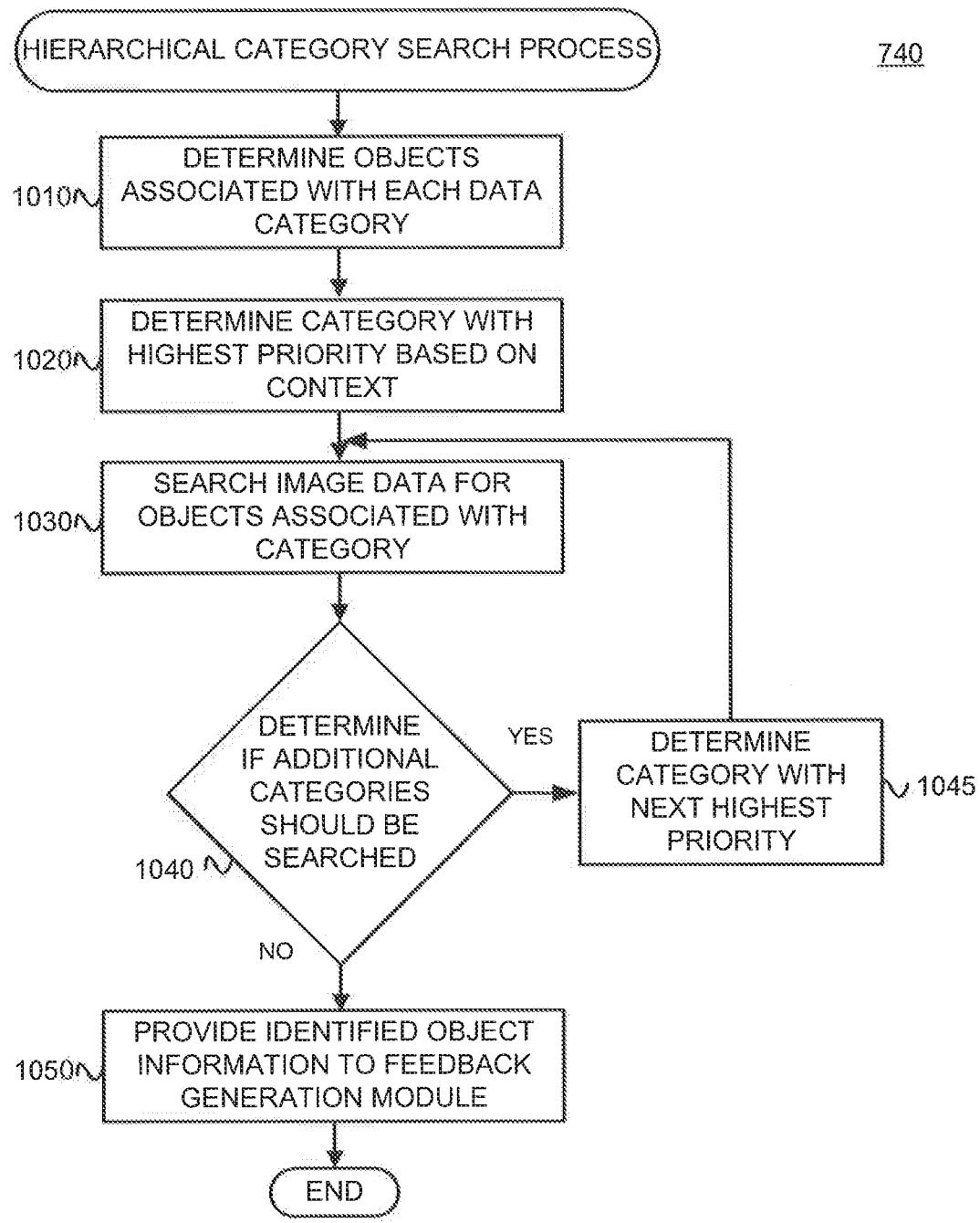
FIG. 10 is an example of a hierarchical category search process, consistent with disclosed embodiments.

FIG. 10 illustrates an example hierarchical category search process, such as that described above in association with Step 740 of process 700 consistent with certain disclosed embodiments. Process 740, as well as any or all of the individual steps therein, may be performed by various aspects of device 110, such as sensory unit 120, processing unit 140, support 210, or any subcomponents therein. For exemplary purposes, FIG. 10 is described as being performed by processor 540, executing software instructions stored within memory 520.

Processor 540 may determine one or more objects associated with each category recognized by trigger identification module 602 (Step 1010). In some embodiments, the determination may be made initially when apparatus 110 is first configured. In other embodiments, apparatus 110 may prompt user 100 to determine the objects associated with each category. Some objects may be associated with a single category, such as, for example, public transportation vehicles. Other objects may be associated with multiple categories.

Based on the particular context, processor 540 may determine the category of data with the highest priority (Step 1020). For example, in the "crossing the street" scenario presented previously, the "warning of risks" category may be ranked highest due to the risks posed to user 100. In other embodiments, other categories may be given the highest priority. For example, if user 100 is operating apparatus 110 at a train station, and apparatus 110 recognizes the landscape as such, a category involving "public transit vehicles" may be given the highest priority to assist user 100 in identifying the correct train to board.

Processor 540 may search the received real-time image data for known objects associated with the chosen category (Step 1030). Processor 540 may call database comparison module 604 to search database(s) 605 for the desired objects. In some embodiments, database comparison module 604 may be configured to search the chosen category until all objects associated with the category have been exhausted. In other embodiments, database comparison module 604 may be configured to search the chosen category for a pre-determined period of time. Further, database comparison module 604 may also be configured to search the category until any item in the environment is identified.

After either the chosen category is exhausted or the pre-determined period of time has elapsed, database comparison module 604 may determine if additional categories should be searched (Step 1040). Additional searching may be necessary if the previous category did not result in any matches with objects in the received real-time image data. In these embodiments, database comparison module 604 may be configured to execute a second search. In some embodiments, an object may be identified that is associated with the first category, but apparatus 110 may be configured to identify more than one object in the environment, or may want to search a secondary category to clarify and confirm context of the identification. In these embodiments, processor 540, via database comparison module 604, may be configured to execute the second search in the second category only after an object from the first category is identified during the first search. In some embodiments, processor 540 may be configured to execute the first search and the second search sequentially.

If additional categories are determined to need searching by database comparison module 604 (Step 1040:YES), then processor 540 may determine the category of data with the next highest priority for the given hand trigger information and context information associated with the current system status (Step 1045). Once the next category to be searched is determined, processor 540 may repeat Steps 1030 and 1040 as many times as is necessary or desired. For example, after initiating the first search of the first category, database comparison module 604 may execute a second search in the image data to identify at least a second object from the second category. In some embodiments, the first and second categories are overlapping or otherwise related. In other embodiments, the first and second categories are different. In some embodiments, the processor may be configured to repetitively execute the first search and the second search until at least one object from one or both of the categories is identified. In some embodiments, third and even fourth categories may be searched. Depending on context, these categories may include, for example, lists of branded products (to assist with identification), text to be read, spatial guidance, text in the wild (i.e. not on an item held or otherwise controlled by user 100), or scene identification.

Alternatively, processor 540 may determine that all proper objects are identified, and that no further categories require search (Step 1040:NO). In these embodiments, processor 540 may provide information about the identified object or objects to feedback generation module 601 (Step 1050). The information may include, as non-limiting examples, the identity of the object, the location of the object, the size of the object, the "status" of the object (e.g., what color is a stoplight), and so on. Upon receipt of the identified object information, feedback generation module 601 may generate feedback to user 100, in a process that will be described below in further detail.

Additionally, processor 540 may call action execution module 603 to execute one or more category-based alternative actions associated with the chosen category or categories, and their associated triggers and contexts. In some embodiments, action execution module performs such alternative actions in addition to the audible feedback generated by feedback generation module 601. In other embodiments, the alternative actions are performed instead of the feedback generation. Alternative actions may include, but not be limited to, reading text, sending an electronic message or instant message over the Internet; configuring settings for apparatus 110 or image sensor 350; activating a user interface, which may appear within the field of view of user 100 and provide additional interactivity options, etc.

Figure 11:
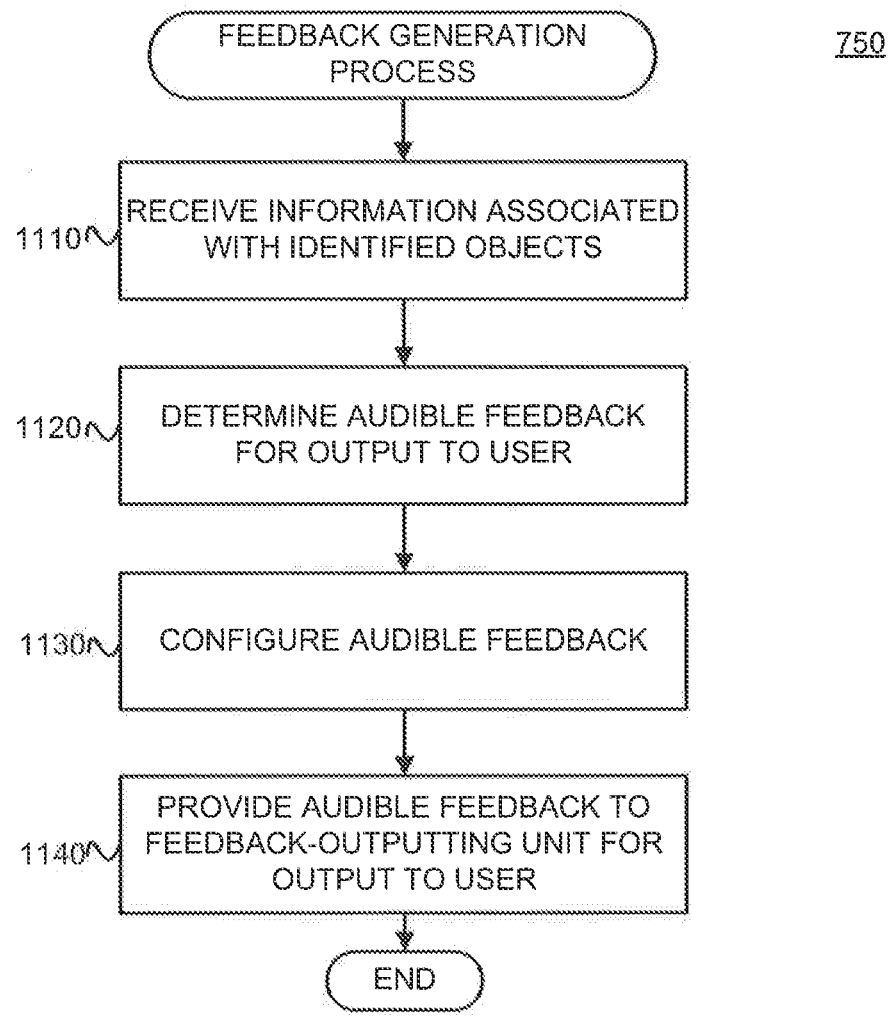
FIG. 11 is an example of a feedback generation process, consistent with disclosed embodiments.

FIG. 11 illustrates an example of a feedback generation process, such as that described above in association with Step 750 of process 700 consistent with certain disclosed embodiments. Process 750, as well as any or all of the individual steps therein, may be performed by various aspects of device 110, such as sensory unit 120, processing unit 140, support 210, or any subcomponents therein. For exemplary purposes, FIG. 11 is described as being performed by processor 540, executing software instructions stored within memory 520.

As discussed above, processor 540, via feedback generation module 601, may receive information associated with one or more identified objects that have been determined to be present in the environment surrounding user 100 (Step 1110). Based on the received information, feedback generation module 601 may determine audible feedback for output to user 100 (Step 1120). In some embodiments, the identified object may already be associated with an audible feedback file stored in memory 520 or database(s) 605. In these embodiments, feedback generation module 601 may simply access the existing associated audible feedback file and prepare it for transmission. In other embodiments, there may be multiple audible feedback files associated with the identified object(s), and feedback generation module may review the determined trigger and/or context information to determine the correct associated audible feedback to output to user 100. In still other embodiments, there may be no existing audible feedback associated with the identified object or objects. In these embodiments, feedback generation module 601 may determine content for audible feedback by prompting user 100 for the feedback, or may infer proper audible feedback, based on context and based on other objects within the category.

Upon determining the proper audible feedback to use, feedback generation module 601 may configure the audible feedback into a readable format, if necessary (Step 1130), then provide the audible feedback to feedback-outputting unit 430 for output to user 100 (Step 1140). Feedback generation module 601 may provide the feedback to feedback-outputting unit 430 via wire 130, or alternatively, via wireless transceiver(s) 530.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for providing environmental information to a visually-impaired user, the apparatus comprising:
    a portable image sensor configured to be worn by the visually-impaired user and to capture real time image data from an environment of the visually-impaired user; and
    at least one portable processor device configured to:
        receive the image data and identify a hand-related trigger in the image data;
        after identifying the hand-related trigger,
        execute a first search in the image data to identify at least a first object from a first category of objects, wherein the first object is identified based on the hand-related trigger in the image data;
        after initiating the first search, execute a second search in at least one of the image data or results from the first search to identify at least a second object from a second category of objects, differing from the first category of objects; and
        cause audible feedback to be output to the visually-impaired user, wherein the audible feedback includes information related to at least one of the first and second objects identified in the image data.

2. The apparatus of claim 1, wherein the at least one processor device is further configured to execute the second search when no object from the first category is identified during the first search.

3. The apparatus of claim 1, wherein the at least one processor device is further configured to execute the second search only after an object from the first category is identified during the first search.

4. The apparatus of claim 1, wherein the at least one processor device is further configured to execute the first search and the second search sequentially.

5. The apparatus of claim 1, wherein the at least one processor device is further configured to:
    identify in the image data a particular context; and
    use the particular context to select the first category of objects and the second category of objects from a plurality of categories of objects.

6. The apparatus of claim 1, wherein the at least one processor device is further configured to repetitively execute the first search and the second search until at least one object is identified.

7. The apparatus of claim 1, wherein the at least one processor device is further configured to execute multiple category-based alternative actions, and after identifying an object from a particular category execute a category-based action associated with the particular category.

8. The apparatus of claim 1, wherein the first search includes searching for objects that prompt audible warnings of risks and the second search includes searching for objects that prompt audible identification of objects.

9. The apparatus of claim 1, wherein the at least one processor device is further configured to execute at least one additional search in the image data to identify an object from at least one other category of objects.

10. The apparatus of claim 9, wherein the at least one processor device is further configured to cause hierarchical searching based on categories, and wherein the categories include at least three of the following: spatial guidance, warning of risks, objects to be identified, text to be read, scene identification, and text in the wild.

11. The apparatus of claim 1, wherein the first category of objects includes at least one of: a bus, a taxi, a train, a traffic light, a sidewalk, and a pedestrian crossing.

12. The apparatus of claim 11, wherein the second category of objects includes a landscape previously recorded by the visually-impaired user.

13. The apparatus of claim 12, wherein the at least one processor device is further configured to identify a third object from a third category of objects, wherein the third category includes branded products.

14. The apparatus of claim 12, wherein the at least one processor device is further configured to identify a third object from a third category of objects, wherein the third category includes text.

15. An apparatus for providing environmental information to a user, the apparatus comprising:
    an image sensor configured to be worn by the user and to capture real time image data from an environment of the user; and
    at least one processor device configured to:
        receive the image data from the image sensor;
        execute, after identifying a hand-related trigger in the image data, a first search in the image data in an attempt to identify a first object from a first category of objects wherein the first object is identified based on the hand-related trigger in the image data;
        execute a second search in the image data in an attempt to identify a second object from a second category of objects, differing from the first category of objects;
        execute a third search in the image data in an attempt to identify a third object from a third category of objects, differing from the first category of objects and the second category of objects;
        execute a fourth search in the image data in an attempt to identify a fourth object from a fourth category of objects, differing from the first category of objects, the second category of objects, and the third category of objects;
        execute an action associated with at least one of: the first object, the second object, the third object, and the fourth object identified in the image data; and
        cause audible feedback to be output, wherein the audible feedback includes information related to an identified object.

16. The apparatus of claim 15, wherein the at least one processor device is further configured to identify the hand-related trigger in the image data.

17. The apparatus of claim 15, wherein the apparatus further comprises a user interface and the at least one processor device is further configured to identify the hand-related trigger based on input received via the user interface.

18. The apparatus of claim 15, wherein the third search is initiated after the second search and the second search is initiated after the first search.

19. The apparatus of claim 15, wherein the at least one processor device is further configured to execute the second search when no object from the first category is identified during the first search, to execute the third search when no object from the second category is identified during the second search, and to execute the fourth search when no object from the third category is identified during the third search.

20. The apparatus of claim 15, wherein the at least one processor device is further configured to execute the second search only after an object from the first category is identified during the first search.

21. A method for providing environmental information to a visually-impaired user, the method comprising:
 identifying a hand-related trigger in captured image data;
 after identifying the hand-related trigger,
 executing a first search in the image data in an attempt to identify at least one object from a first category of objects, wherein the first object is identified based on the hand-related trigger in the image data;
 after initiating the first search, executing a second search in the image data in an attempt to identify at least one object from a second category of objects, differing from the first category of objects; and
 outputting audible feedback to the visually-impaired user, wherein the audible feedback includes information related to an object identified in the image data.

22. A software product stored on a non-transitory computer readable medium and comprising data and computer implementable instructions for carrying out the method of claim 21.

23. An apparatus for providing environmental information to a visually-impaired user, the apparatus comprising:
 a portable image sensor configured to be worn by the visually-impaired user and to capture real time image data from an environment of the visually-impaired user; and
 at least one portable processor device configured to:
  receive the image data and identify a hand-related trigger in the image data;
  after identifying the hand-related trigger, identify at least one object in the image data based on the hand-related trigger in the image data;
  determine first information related to the at least one object identified in the image data;
  cause first audible feedback to be output to the visually-impaired user, wherein the first audible feedback comprises the first information related to the at least one object identified in the image data;
  determine, after identifying that the hand-related trigger remains associated with the at least one object for a predetermined period of time, second information related to the at least one object identified in the image data; and
  cause second audible feedback to be output to the visually-impaired user, wherein the second audible feedback includes the second information related to at least the first object identified in the image data.

24. The apparatus of claim 23, wherein the at least one processor device is further configured to:
 identify in the image data a particular context;
 use the particular context to determine information about at least the first object identified in the image data that is of the highest priority;
 determine the first information based at least on the highest priority information;
 use the particular context to determine information about at least the first object identified in the image data that is of the next highest priority; and
 determine the second information based at least on the next highest priority information.

25. The apparatus of claim 23, wherein the at least one processor device is further configured to identify at least one additional object in the image data based on the hand-related trigger in the image data.

* * * * *